US008105811B2

(12) United States Patent
Jeffries et al.

(10) Patent No.: US 8,105,811 B2
(45) Date of Patent: Jan. 31, 2012

(54) SUGAR TRANSPORT SEQUENCES, YEAST STRAINS HAVING IMPROVED SUGAR UPTAKE, AND METHODS OF USE

(75) Inventors: Thomas William Jeffries, Madison, WI (US); JuYun Bae, Madison, WI (US); Bernice Chin-yun Lin, Cupertino, CA (US); Jennifer Rebecca Headman Van Vleet, Visalen, CA (US)

(73) Assignees: Wisconsin Alumni Research Foundation, Madison, WI (US); The United States of America as represented by the Secretary of Agriculture, Washington, DC (US)

( * ) Notice: Subject to any disclaimer, the term of this patent is extended or adjusted under 35 U.S.C. 154(b) by 235 days.

(21) Appl. No.: 12/484,714

(22) Filed: Jun. 15, 2009

(65) Prior Publication Data

US 2009/0325241 A1    Dec. 31, 2009

Related U.S. Application Data

(60) Provisional application No. 61/061,417, filed on Jun. 13, 2008.

(51) Int. Cl.
*C12P 7/06* (2006.01)
*C12N 1/14* (2006.01)
*C12N 15/00* (2006.01)
*C07H 21/02* (2006.01)

(52) U.S. Cl. .............. 435/161; 435/69.1; 435/320.1; 435/255.1; 435/255.5; 536/23.1

(58) Field of Classification Search .......... 435/105, 435/252.3, 320.1, 161, 255.1, 255.5; 536/23.1
See application file for complete search history.

(56) References Cited

U.S. PATENT DOCUMENTS 4,701,414 A    10/1987    Van Dijken et al.

OTHER PUBLICATIONS

Nature Biotechnology 25: 319-326 (Mar. 4, 2007, published on line).*
Nature Biotechnology 25: 319-326 (Mar. 4, 2007, published on line)—Supplementary Fig.1.*
Weierstall, Thomas, et al., Cloning and characterization of three genes (SUT1-3) encoding glucose transporters of the yeast Pichia stipitis, Molecular Microbiology, 1999, 871-883, 31(3), Blackwell Science Ltd, Dusseldorf, Germany.
Hamacher, Tanja, et al., Characterization of the xylose-transporting properties of yeast hexose transporters and their influence on xylose utilization, Microbiology, 2002, 2783-2788, 148, SGM, Great Britain.
Amore et al.; UniProtKB/Swiss-Prot. P31867 [online] Mar. 2, 2010 (retrieved Aug. 25, 2011) Available on the internet:, URL: http://www.uniprot.org/uniprot/P31867.txt?version =65.
Jeffries, Thomas W. et al.; "Pichia stipitis genomics, transcriptomics, and gene clusters"; 2009, *FEMS Yeast Res.*, vol. 9, No. 6, pp. 793-807.
Jeffries, Thomas W. et al.; UniProtKB/TrEMBL. A3GIF0 [online] Mar. 2, 2010 (retrieved Aug. 25, 2011). Available on the internet: <URL: http://www.uniprot.org/uniprot/A3GIF0.txt?version=24.
Jeffries, Thomas W. et al.; UniProtKB/TrEMBL. A3M0D0 [online] Mar. 2, 2010 (retrieved Aug. 25, 2011). Available on the internet: <URL: http://www.uniprot.org/uniprot/A3M0D0.txt?version=28.
Jeffries, Thomas W. et al.; UniProtKB/TrEMBL. A3GF74 [online] Mar. 2, 2010 (retrieved Aug. 25, 2011). Available on the internet: <URL: http://www.uniprot.org/uniprot/A3GF74.txt?version=22.
Koetter et al.; UniProtKB/Swiss-Prot. P22144 [online] Mar. 2, 2010 (retrieved Aug. 25, 2011). Available on the internet: <URL: http://www.uniprot.org/uniprot/P22144.txt?version=69.

* cited by examiner

*Primary Examiner* — Tekchand Saidha
(74) *Attorney, Agent, or Firm* — Kilpatrick Townsend & Stockton LLP

(57) ABSTRACT

Disclosed are nucleic acid constructs comprising coding sequences operably linked to a promoter not natively associated with the coding sequence. The coding sequences encode *Pichia stipitis* proteins that allow recombinant strains of *Saccharomyces cerevisiae* expressing the protein to grow on xylose, and allow or increase uptake of xylose by *Pichia stipitis* or *Saccharomyces cerevisiae* expressing the coding sequences. Expression of the coding sequences enhances uptake of xylose and/or glucose, allowing increased ethanol or xylitol production.

19 Claims, 8 Drawing Sheets

```
ClustalW (v1.4) multiple sequence alignment

3 Sequences Aligned          Alignment Score = 34227
Gaps Inserted = 0            Conserved Identities = 1606

Pairwise Alignment Mode: Slow
Pairwise Alignment Parameters:
    Open Gap Penalty = 10.0   Extend Gap Penalty = 0.1

Multiple Alignment Parameters:
    Open Gap Penalty = 10.0   Extend Gap Penalty = 0.1
    Delay Divergent = 40%     Transitions: Weighted Processing time: 3.3 seconds SUT4 ORF           1 ATGTCCTCACAAGATTTACCCTCGGGTGCTCAAACCCCAATCGATGGTTC    50
(SEQ ID NO:3)
SUT2.nt.mv         1 ATGTCCTCACAAGATTTACCCTCGGGTGCTCAAACCCCAATCGATGGTTC    50
(SEQ ID NO:12)
sut3               1 ATGTCCTCACAAGATTTACCCTCGGGTGCTCAAACCCCAATCGATGGTTC    50
(SEQ ID NO:13)
                     **************************************************

SUT4 ORF          51 TTCCATCCTCGAAGATAAAGTTGAGCAAAGTTCGTCCTCAAATAGCCAAA   100
SUT2.nt.mv        51 TTCCATCCTCGAAGATAAAGTTGAGCAAAGTTCGTCCTCAAATAGCCAAA   100
sut3              51 TTCCATCCTCGAAGATAAAGTTGAGCAAAGTTCGTCCTCAAATAGCCAAA   100
                     **************************************************

SUT4 ORF         101 GTGATTTAGCTTCTATTCCAGCAACAGGTATCAAAGCCTATCTCTTGGTT   150
SUT2.nt.mv       101 GTGATTTAGCTTCCATTCCAGCAACAGGTATCAAAGCCTATCTCTTGGTT   150
sut3             101 GTGATTTAGCTTCCATTCCAGCAACAGGTATCAAAGCCTATCTCTTGGTT   150
                     ************* ************************************

SUT4 ORF         151 TGTTTCTTCTGCATGTTGGTTGCCTTCGGTGGCTTCGTATTCGGTTTCGA   200
SUT2.nt.mv       151 TGTTTCTTCTGCATGTTGGTTGCCTTTGGTGGATTCGTATTCGGTTTCGA   200
sut3             151 TGTTTCTTCTGCATGTTGGTTGCCTTTGGTGGCTTCGTATTCGGTTTCGA   200
                     ************************** ***** *****************

SUT4 ORF         201 TACCGGTACTATTTCCGGTTTCCTTAATATGTCTGATTTCCTTTCCAGAT   250
SUT2.nt.mv       201 TACCGGTACAATTTCCGGTTTCCTTAATATGTCTGATTTCCTTTCCAGAT   250
sut3             201 TACCGGTACAATTTCCGGTTTCCTTAATATGTCTGATTTCCTTTCCAGAT   250
                     ********* ****************************************

SUT4 ORF         251 TTGGTCAAGATGGTTCTGAAGGAAAATATTTGTCTGATATCAGAGTCGGT   300
SUT2.nt.mv       251 TTGGTCAAGATGGTTCTGAAGGAAAATATTTGTCTGATATCAGAGTCGGT   300
sut3             251 TTGGTCAAGATGGTTCTGAAGGAAAATATTTGTCTGATATCAGAGTCGGT   300
                     **************************************************

SUT4 ORF         301 TTGATTGTTTCCATTTTTAACATTGGTTGTGCAATTGGTGGTATTTTCCT   350
SUT2.nt.mv       301 TTGATTGTTTCCATTTTTAACATTGGTTGTGCAATTGGTGGTATTTTCCT   350
sut3             301 TTGATTGTTTCCATTTTTAACATTGGTTGTGCAATTGGTGGTATTTTCCT   350
                     **************************************************

SUT4 ORF         351 TTCTAAGATAGGAGATGTTTACGGTAGAAGAATTGGTATCATTTCAGCTA   400
SUT2.nt.mv       351 TTCTAAGATAGGAGATGTTTACGGTAGAAGAATTGGTATCATTTCAGCTA   400
sut3             351 TTCTAAGATAGGAGATGTTTACGGTAGAAGAATTGGTATCATTTCAGCTA   400
                     **************************************************

SUT4 ORF         401 TGGTTGTCTATGTCGTCGGTATAATCATCCAGATCTCGTCCCAAGATAAG   450
SUT2.nt.mv       401 TGGTTGTCTACGTCGTCGGTATTATCATCCAGATCTCGTCCCAAGACAAG   450
sut3             401 TGGTTGTATACGTCGTCGGTATTATCATCCAGATCTCGTCCCAAGACAAG   450
                     ******* ** *********** *********************** ***

SUT4 ORF         451 TGGTATCAACTTACAATTGGACGTGGAGTTACAGGATTAGCTGTTGGTAC   500
SUT2.nt.mv       451 TGGTACCAACTTACAATTGGACGTGGAGTTACAGGATTAGCTGTTGGTAC   500
```

FIG. 1 (1 of 3)

```
sut3         451  TGGTACCAACTTACAATTGGACGTGGAGTTACAGGATTAGCTGTTGGTAC  500
                  **** ********************************************

SUT4 ORF     501  TGTTTCCGTTTTGTCTCCAATGTTCATTAGTGAAAGTGCTCCCAAGCATT  550
SUT2.nt.mv   501  TGTTTCAGTGTTGTCTCCAATGTTCATTAGTGAAAGTGCTCCAAAGCATT  550
sut3         501  TGTTTCAGTGTTGTCTCCAATGTTCATTAGTGAAAGTGCTCCAAAGCATT  550
                  ****** ** ******************************** *******

SUT4 ORF     551  TGAGAGGTACTTTGGTATACTGTTACCAATTATGCATCACCTTAGGTATT  600
SUT2.nt.mv   551  TGAGAGGTACTTTGGTATACTGTTACCAATTATGTATCACCTTAGGTATT  600
sut3         551  TGAGAGGTACTTTGGTATACTGTTACCAATTATGTATCACCTTAGGTATT  600
                  ********************************** ***************

SUT4 ORF     601  TTCATTGGTTACTGTGTCACTTATGGAACCAAAGATTTAAATGATTCAAG  650
SUT2.nt.mv   601  TTCATTGGTTACTGTGTCACTTATGGAACCAAAGATTTAAATGATTCAAG  650
sut3         601  TTCATTGGTTACTGTGTCACTTATGGAACCAAAGATTTAAATGATTCAAG  650
                  **************************************************

SUT4 ORF     651  ACAATGGAGAGTTCCTTTGGGTTTATGTTTCCTTTGGGCTATTTTCTTAG  700
SUT2.nt.mv   651  ACAATGGAGAGTTCCTTTGGGTTTATGTTTCCTTTGGGCTATTTTCTTAG  700
sut3         651  ACAATGGAGAGTTCCTTTGGGCTTATGCTTCCTTTGGGCTATTTTCTTAG  700
                  ********************* ***** **********************

SUT4 ORF     701  TTGTTGGTATGTTGGCTATGCCAGAATCCCCAAGATTCTTGATTGAAAAG  750
SUT2.nt.mv   701  TTGTCGGTATGTTGGCTATGCCTGAATCCCCAAGATTCTTAATTGAAAAG  750
sut3         701  TTGTCGGTATGTTGGCTATGCCAGAATCCCCAAGATTCTTAATTGAAAAG  750
                  **** ***************** ***************** *********

SUT4 ORF     751  AAGAGAATCGAAGAAGCCAAGAAGTCCCTTGCAAGATCCAACAAGTTGTC  800
SUT2.nt.mv   751  AAGAGAATCGAAGAAGCCAAGAAGTCCCTTGCAAGATCCAACAAGTTATC  800
sut3         751  AAGAGAATCGAAGAAGCCAAGAAGTCCCTTGCAAGATCCAACAAGTTATC  800
                  *********************************************** **

SUT4 ORF     801  TCCAGAAGATCCAGGTGTCTACACTGAAGTTCAATTGATTCAAGCTGGTA  850
SUT2.nt.mv   801  TCCAGAAGATCCAGGTGTCTACACTGAAGTTCAATTGATTCAGGCTGGTA  850
sut3         801  TCCGGAAGATCCAGGTGTCTACACTGAATTTCAATTGATTCAGGCTGGTA  850
                  *** ************************ ************* *******

SUT4 ORF     851  TTGACAGAGAAGCTGCTGCAGGTTCTGCTTCGTGGATGGAATTGATTACC  900
SUT2.nt.mv   851  TTGACAGAGAAGCTGCTGCAGGTTCTGCTTCATGGATGGAATTGATCACT  900
sut3         851  TTGACAGAGAAGCTGCTGCAGGTTCTGCTTCGTGGATGGAATTGATCACT  900
                  ******************************* ************** **

SUT4 ORF     901  GGTAAACCAGCTATTTTCAGAAGAGTTATCATGGGAATTATCTTACAGTC  950
SUT2.nt.mv   901  GGTAAGCCAGCTATTTTCAGAAGAGTTATCATGGGAATTATCTTACAGTC  950
sut3         901  GGTAAGCCAGCTATTTTCAGAAGAGTTATCATGGGAATTATCTTGCAGTC  950
                  ***** ************************************** *****

SUT4 ORF     951  TTTGCAGCAATTAACTGGTGTCAACTATTTCTTCTACTACGGAACTACAA 1000
SUT2.nt.mv   951  TTTGCAACAATTAACTGGTGTCAACTATTTCTTCTATTACGGAACTACAA 1000
sut3         951  TTTGCAACAATTAACTGGTGTCAACTATTTCTTCTATTACGGAACTACAA 1000
                  ****** ***************************** *************

SUT4 ORF    1001  TCTTCCAAGCTGTTGGTTGCAAGATTCCTTCCAGACTTCCATCATCTTA  1050
SUT2.nt.mv  1001  TCTTCCAAGCTGTTGGTTGCAAGATTCCTTCCAGACTTCCATCATCTTA  1050
sut3        1001  TCTTCCAAGCTGTTGGTTGCAAGATTCCTTCCAGACTTCCATCATCTTA  1050
                  *************************************************

SUT4 ORF    1051  GGTACAGTCAACTTTCTTTCTACATTTGTTGGTATTTGGGCCATTGAAAG 1100
SUT2.nt.mv  1051  GGTACAGTCAACTTTCTTTCTACATTTGTTGGTATTTGGGCCATTGAAAG 1100
sut3        1051  GGTACAGTCAACTTTCTTTCTACATTTGTTGGTATTTGGGCCATTGAAAG 1100
                  **************************************************

SUT4 ORF    1101  ATTTGGAAGAAGACAATGTTTGTTAGTCGGTTCTGCTGGTATGTTCGTTT 1150
SUT2.nt.mv  1101  ATTTGGAAGAAGACAATGTTTGTTAGTCGGTTCTGCTGGTATGTTCGTTT 1150
sut3        1101  ATTTGGAAGAAGACAATGTTTGTTAGTCGGTTCTGCTGGTATGTTCGTTT 1150
```

FIG. 1 (2 of 3)

```
                  **************************************************
SUT4 ORF    1151  GTTTCATCATTTACTCTGTCATTGGTACAACTCATTTGTTCATTGATGGA  1200
SUT2.nt.mv  1151  GTTTCATCATTTACTCCGTTATTGGTACAACTCATTTGTTCATTGATGGA  1200
sut3        1151  GTTTCATCATTTACTCCGTTATTGGTACAACTCATTTGTTCATTGATGGA  1200
                  ***************  **  *****************************

SUT4 ORF    1201  GTAGTAGATAACGACAACACCCGTCAACTGTCTGGTAATGCTATGATCTT  1250
SUT2.nt.mv  1201  GTAGTAGATAACGACAACACCCGTCAACTGTCTGGTAATGCTATGATCTT  1250
sut3        1201  GTAGTAGATAACGACAACACCCGTCAACTGTCTGGTAATGCTATGATCTT  1250
                  **************************************************

SUT4 ORF    1251  TATCACTTGTTTGTTCATCTTCTTCTTTGCCTGTACTTGGGCTGGAGGTG  1300
SUT2.nt.mv  1251  TATCACTTGTTTGTTCATCTTCTTCTTTGCCTGTACATGGGCTGGAGGTG  1300
sut3        1251  TATCACTTGTTTGTTCATCTTCTTCTTTGCCTGTACATGGGCTGGAGGTG  1300
                  ************************************ *************

SUT4 ORF    1301  TTTTTACAATCATTTCCGAATCATATCCATTGAGAATCAGATCCAAGGCT  1350
SUT2.nt.mv  1301  TTTTTACCATCATTTCCGAATCATATCCATTGAGAATCAGATCCAAGGCA  1350
sut3        1301  TTTTTACCATCATTTCCGAATCATATCCATTGAGAATCAGATCCAAGGCA  1350
                  ******* *****************************************

SUT4 ORF    1351  ATGTCTATTGCCACTGCCGCTAACTGGATGTGGGGTTTCTTGATTTCATT  1400
SUT2.nt.mv  1351  ATGTCTATTGCTACTGCTGCTAACTGGATGTGGGGCTTCTTGATTTCCTT  1400
sut3        1351  ATGTCTATTGCTACTGCTGCTAACTGGATGTGGGGCTTCTTGATTTCCTT  1400
                  *********** ***** ***************** ***********  **

SUT4 ORF    1401  CTGCACTCCATTCATTGTTAACGCCATCAACTTCAAGTTCGGCTTTGTGT  1450
SUT2.nt.mv  1401  CTGCACTCCATTCATTGTTAATGCCATCAACTTCAAGTTCGGCTTTGTGT  1450
sut3        1401  CTGCACTCCATTCATTGTTAATGCCATCAACTTCAAGTTCGGCTTTGTGT  1450
                  ********************* ****************************

SUT4 ORF    1451  TTACTGGTTGTTTGCTCTTTTCGTTCTTCTATGTCTACTTCTTTGTCAGC  1500
SUT2.nt.mv  1451  TTACTGGTTGTTTACTCTTTTCGTTCTTCTATGTCTACTTCTTTGTCAGC  1500
sut3        1451  TTACTGGTTGTTTACTCTTTTCGTTCTTCTATGTCTACTTCTTTGTCAGC  1500
                  ************* ************************************

SUT4 ORF    1501  GAAACCAAAGGTTTGTCGTTGGAAGAAGTTGATGAGTTGTACGCTGAGGG  1550
SUT2.nt.mv  1501  GAAACCAAAGGTTTGTCGTTGGAAGAAGTTGATGAGTTGTACGCTGAAGG  1550
sut3        1501  GAAACCAAAGGTTTGTCGTTGGAAGAAGTTGATGAGTTGTACGCTGAAGG  1550
                  *********************************************** **

SUT4 ORF    1551  AATTGCACCATGGAAATCCGGTGCATGGGTTCCTCCTTCTGCACAACAAC  1600
SUT2.nt.mv  1551  TATTGCACCATGGAAGTCTGGTGCATGGGTTCCTCCTTCTGCCCAACAAC  1600
sut3        1551  TATTGCACCATGGAAGTCTGGTGCATGGGTTCCTCCTTCTGCCCAACAAC  1600
                  ************* ** *************************  *******

SUT4 ORF    1601  AAATGCAAAACTCTACTTATGGTGCCGAAACAAAAGAGCAAGAGCAAGTT  1650
SUT2.nt.mv  1601  AAATGCAAAACTCCACTTATGGTGCCGAAGCAAAAGAGCAAGAGCAAGTT  1650
sut3        1601  AAATGCAAAACTCCACTTATGGTGCCGAAGCAAAAGAGCAAGAGCAAGTT  1650
                  ************* ************** *********************

SUT4 ORF    1651  TAG    1653  ++++    34 NT changes
SUT2.nt.mv  1651  TAG    1653  ++       3 NT changes
sut3        1651  TAGSTT 1656  +++      6 NT changes
                  ***
```

FIG. 1 (3 of 3)

50 mM $^{14}$C-glucose or xylose uptake with time course.

US 8,105,811 B2

SUGAR TRANSPORT SEQUENCES, YEAST STRAINS HAVING IMPROVED SUGAR UPTAKE, AND METHODS OF USE

CROSS-REFERENCE TO RELATED APPLICATIONS

This application claims the priority to U.S. Provisional Patent Application No. 61/061,417 filed Jun. 13, 2008, which is incorporated by reference herein.

STATEMENT REGARDING FEDERALLY SPONSORED RESEARCH OR DEVELOPMENT

This invention is jointly owned between WARF and the USDA and was made with United States government support awarded by the following agencies:

USDA Grant Number 2006-35504-17436.

The government has certain rights in this invention.

BACKGROUND OF THE INVENTION

Within the United States, ongoing res is directed toward developing alternative energy sources to reduce our dependence on foreign oil and nonrenewable energy. The use of ethanol as a fuel has become increasingly prevalent in recent years. Currently, corn is the primary carbon source used in ethanol production. The use of corn in ethanol production is not economically sustainable and, arguably, may result in increased food costs.

In order to meet the increased demand for ethanol, it will be necessary to ferment sugars from other biomass, such as agricultural wastes, corn hulls, corncobs, cellulosic materials, pulping wastes, fast-growing hardwood species, and the like. Biomass from most of these sources contains large amounts of xylose, constituting about 20 to 25% of the total dry weight. Because agricultural residues have a high xylose content, the potential economic and ecologic benefits of converting xylose in these renewable materials to ethanol are significant.

In biomass conversion, microorganisms serve as biocatalysts to convert cellulosic materials into usable end products such as ethanol. Efficient biomass conversion in large-scale industrial applications requires a microorganism that can tolerate high sugar and ethanol concentrations, and which is able to ferment multiple sugars simultaneously.

The pentose D-xylose is significantly more difficult to ferment than D-glucose. Bacteria can ferment pentoses to ethanol and other co-products, and bacteria with improved ethanol production from pentose sugars have been genetically engineered. However, these bacteria are sensitive to low pH and high concentrations of ethanol, their use in fermentations is associated with co-product formation, and the level of ethanol produced remains too low to make the use of these bacteria in large-scale ethanol production economically feasible.

In general, industrial producers of ethanol strongly favor using yeast as biocatalysts, because yeast fermentations are relatively resistant to contamination, are relatively insensitive to low pH and ethanol, and are easier to handle in large-scale processing. Many different yeast species use xylose respiratively, but only a few species use xylose fermentatively. Fermentation of xylose to ethanol by wild type xylose-fermenting yeast species occurs slowly and results in low yields, relative to fermentation rates and ethanol yields that are obtained with conventional yeasts in glucose fermentations.

In order to improve the cost effectiveness of xylose fermentation, it is necessary to increase the rate of fermentation and the ethanol yields obtained.

The most commonly used yeast in industrial applications is *Saccharomyces cerevisiae*. Although *S. cerevisiae* is unable to grow on or ferment xylose, homogenates of *S. cerevisiae* can readily ferment D-ribulose-5-phosphate to ethanol, and can convert D-xylulose-5-phosphate to a lesser extent. *S. cerevisiae* metabolically engineered to overproduce D-xylose reductase (XYL1), xylitol dehydrogenase (XYL2) and D-xylulokinase (XYL3 or XKS1) or some forms of xylose isomerase (xylA) along with AYL3 or XKS1 can metabolize xylose to ethanol.

*Pichia stipitis* is a yeast species that in its native state is able to ferment xylose to produce ethanol. In *P. stipitis*, fermentative and respirative metabolism co-exist to support cell growth and the conversion of sugar to ethanol.

There is a need in the art for yeast strains having improved ability to convert sugars to ethanol.

BRIEF SUMMARY OF THE INVENTION

In one aspect, the present invention provides a nucleic acid construct comprising a coding sequence operably linked to a promoter not natively associated with the coding sequence. The coding sequence encodes a polypeptide having at least 95% amino acid identity to SEQ ID NO:2, SEQ ID NO:4, or SEQ ID NO:6.

Other aspects of the invention provide yeast strains comprising the nucleic acid construct, and methods of producing ethanol or xylitol by growing a yeast strain of the invention in xylose-containing medium.

BRIEF DESCRIPTION OF THE SEVERAL VIEWS OF THE DRAWINGS

FIG. 1 shows the alignment of PsSUT2, PsSUT3, and PsSUT4.

DETAILED DESCRIPTION OF THE INVENTION

Figure 2:
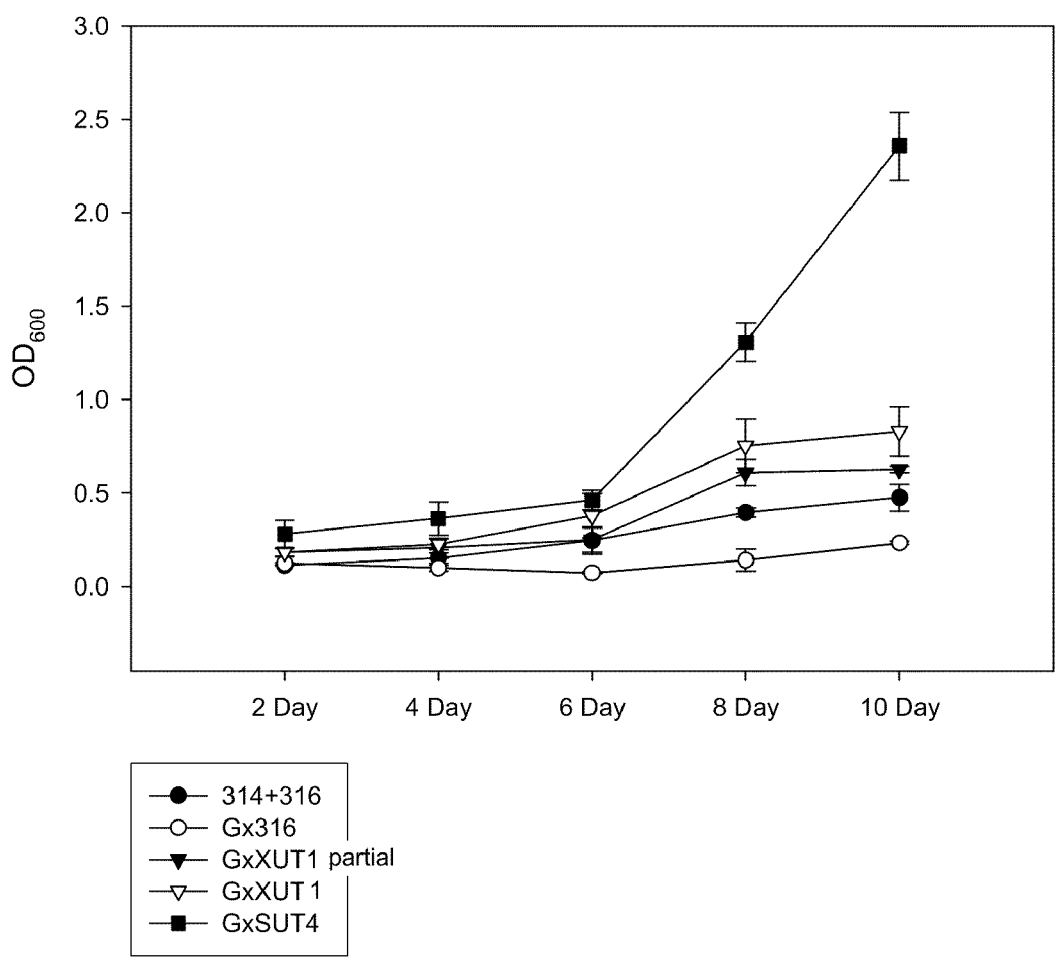
FIG. 2 shows growth, measured as $OD_{600}$, of *S. cerevisiae* expressing XUT1 or SUT4 on xylose as a function of time.

One approach to increasing the efficiency of yeast-catalyzed conversion of sugars to ethanol or to other products such as xylitol is to enhance uptake of sugars by the yeast. Cellulosic and hemicellulosic materials used in fermentation reactions are generally subjected to pretreatments and enzymatic processes that produce a mixture of several sugars, including glucose, xylose, mannose, galactose, and arabinose.

*Saccharomyces cerevisiae* and other hexose-fermenting yeasts have sugar transporters that facilitate uptake of hexoses. Some hexose sugar transporters also promote uptake of pentoses such as xylose, but at a much lower rate and with much lower affinity. Therefore, xylose uptake and utilization is impaired until glucose is consumed. When the substrate includes large initial concentrations of glucose, ethanol production from fermentation of glucose may result in inhibitory concentrations of ethanol before xylose uptake begins.

In order to promote xylose utilization by yeast in fermentation of mixed hemicellulosic sugars, sugar transport proteins having high affinity or specificity for xylose were identified and used to develop yeast engineered to have improved xylose uptake, as described below in the Examples.

The genome of the xylose-fermenting yeast *Pichia stipitis* was examined for putative sugar transporters based on similarity to transporters that facilitate uptake of hexoses, lactose, maltose, phosphate, urea, and other compounds. Eight putative xylose transporters (XUT1-7 and SUT4) were chosen based on their implied structures and sequence similarities to other reported sugar transporters. Genome array expression studies were used to evaluate whether the sugar transporters showed induced expression in cells grown on xylose. Genome array expression results were confirmed using quantitative PCR of transcripts from cells grown on xylose.

Sequences encoding polypeptides corresponding to those encoded by two genes (XUT1 and SUT4) that showed increased expression in cells grown on xylose-containing media under oxygen limited conditions were expressed in a host strain *Saccharomyces cerevisiae* JYB3011, which lacks all hexose-transport genes and expresses *P. stipitis* XYL1, XYL2, and XYL3, which encode xylose reductase (XR), xylitol dehydrogenase (XDH), and xylulokinase (XK), respectively. Expression of either XUT1 or SUT4 allowed growth of the *S. cerevisiae* strain on xylose. Both XUT1 and SUT4 allowed increased xylose uptake. Cells carrying these sequences were tested for their relative affinities in taking up $^{14}$C-labeled glucose or $^{14}$C-labeled xylose. Xut1 was shown to have a higher affinity for xylose, and Sut4 a higher affinity for glucose. A transformant carrying a partial sequence of the XUT1 gene, which encodes the C-terminal portion of the protein, beginning with amino acid residue 154 of SEQ ID NO:2, was shown to bind xylose and glucose but did not accumulate these sugars, thereby demonstrating that at least some portion of the amino terminus of the protein is needed for sugar transport.

Thus, expression of any of XUT1, XUT1 partial, and SUT4 in *Saccharomyces cerevisiae* allows growth on xylose, and in the case of XUT1 and SUT4, uptake of xylose. It is envisioned that expression of any of XUT1, XUT1 partial, and SUT4 or sequences similar to XUT1, XUT1 partial, and SUT4 in other yeast species will also allow growth on xylose and/or uptake of xylose.

The sequence of the deduced amino acid sequence of the putative proteins encoded by the *Pichia stipitis* XUT1 and SUT4 genes are provided in SEQ ID NO:2 and SEQ ID NO:4, respectively. The sequences of the XUT1 and SUT4 coding sequences prepared from *Pichia stipitis* are shown in SEQ ID NO:1 and SEQ ID NO:3, respectively.

The *P. stipitis* glucose/xylose facilitators PsSut1-4 have a high degree of sequence identity, with PsSut1 having 78% amino acid identity with PsSut2, 3, and 4. PsSut2 differs from PsSut3 by one amino acid (L279V). PsSut4 differs from PsSut2 by just one amino acid A544T) and from PsSUT3 by two amino acids (L279V and A544T ). While all four facilitators have similar affinities for glucose, their affinities for xylose were shown to differ significantly (See Table 3). Notably, PsSut4 has a higher specificity ratio ($V_{max}/K_m$) than the other Sut facilitators for glucose and xylose, and a higher affinity for xylose than any of the other facilitators.

It is envisioned that changes to the polypeptides could be made without affecting their activities, and such variations are within the scope of the invention. For example, polypeptides have insertions, deletions or substitutions of amino acids relative to SEQ ID NO:2 and SEQ ID NO:4 are within the scope of the invention, provided that the polypeptide has at least 80% amino acid identity to SEQ ID NO:2 and SEQ ID NO:4. Suitably, a polypeptide according to the invention has at least 85%, 90%, or 95% amino acid identity to SEQ ID NO:2 or SEQ ID NO:4. It is further envisioned that polypeptides according to the invention have at least 80%, 85%, 90%, 95%, 96%, 97%, 98%, 99%, or 100% amino acid identity to SEQ ID NO:4, and have a threonine residue or a serine residue at a position corresponding to amino acid 544 of SEQ ID NO:4. Preferably, polypeptides according to the invention retain their activity, i.e., retain the ability to enhance uptake of glucose and/or xylose. Such activity may be assayed by any suitable means, including, for example, those described in the examples.

It is well understood among those of ordinary skill in the art that certain changes in nucleic acid sequence make little or no difference to the overall function of the protein or peptide encoded by the sequence. Due to the degeneracy of the genetic code, particularly in the third position of codons, changes in the nucleic acid sequence may not result in a different amino acid being specified by that codon. Changes that result in an amino acid substitution may have little or no effect on the three dimensional structure or function of the encoded protein or peptide. Conservative substitutions are even less likely to result in a lost of function. In addition, changes that result in insertions or deletions of amino acids may also be acceptable.

Alignment of the native sequence encoding PsSut4 with those encoding PsSut2 and PsSut3 shows that PsSut4 differs from the coding sequences for PsSut2 and PsSut3 at more than 30 bases (FIG. 1), with only two differences resulting in a change in the amino acid specified. Suitably, polynucleotides according to the invention include one or more of the divergent sequences of PsSUT4 shown in FIG. 1, in any combination. Suitably, the polynucleotides include anywhere from one to all of the divergent sequences of PsSUT4 shown in FIG. 1.

It is expected that expression of more than one of the proteins encoded by the polynucleotides of the invention, as exemplified by SEQ ID NO:2, SEQ ID NO:4, and SEQ ID NO:6, could be obtained in a transgenic yeast cell. Expression of two or more polynucleotides of the invention may afford additional advantages in terms of fermentation rate or sugar uptake. For example, one could create a yeast strain that expresses a polynucleotide encoding a polypeptide having at least 80%, at least 85%, at least 90%, or at least 95% amino acid identity to SEQ ID NO:2 together with a polynucleotide encoding a polypeptide having at least 80%, at least 85%, at least 90%, or at least 95% amino acid identity to SEQ ID NO:4.

Additionally, the polynucleotides of the invention may further include a sequence encoding a selectable marker that would allow selection of yeast expressing the polynucleotide.

In the examples, expression of SUT4 under the control of the promoter from *P. stipitis* fatty acid synthase 2 (FAS2 promoter), which is induced by xylose and under oxygen limiting conditions, was obtained in *S. cerevisiae* yJML123 and in *P. stipitis* UC7. The yJML123+SUT4 was able to use both glucose and xylose at a faster rate than the control strain. Neither strain was able to use all of the xylose. The yJML123+SUT4 strain, which has reduced expression of xylitol reductase, produced a higher yield of xylitol (18.45 g/L) than the control strain (15.51 g/L). Further, the yJML123+SUT4 strain produced a higher yield of xylitol faster than the control.

The *P. stipitis* UC7+SUT4 strain was grown under oxygen limiting conditions (50 mL of culture with a starting $OD_{600}$ of 10 in a 125 mL flask aerated at speed of 100 rpm at 30° C.). The UC7+SUT4 strain was found to use xylose at a faster than the UC7 control; neither strain used all of the xylose. The xylitol yield of UC7+SUT4 strain (14.98 g/L) was similar to that of the UC7 control (15.18 g/L). The UC7+SUT4 strain had a higher ethanol specific productivity.

In another example, UC7+SUT4 strain was grown in glucose (7% w/w) and xylose (3% w/w) in a three liter bioreactor. Those results indicated that the UC7+SUT4 grew at a faster rate than did the UC7 control. The UC7+SUT4 strain had a higher biomass yield than the control. Additionally, the ethanol yield was higher for the UC7+SUT4 strain. The UC7+SUT4 strain consumed both glucose and xylose at a higher rate and consumed all of the sugars, whereas the control consumed only 88% of the glucose and did not appear to consume xylose. Finally, the specific rate of ethanol production on a dry cell weight basis was increased by more than three fold.

In the examples, strains were developed by causing nucleic acid of the invention to be introduced into a chromosome of the host yeast strain. This can be accomplished by any suitable means. However, it is envisioned that one could obtain increased expression of the nucleic acid constructs of the invention using an extrachromosomal genetic element, by integrating additional copies, by increasing promoter strength, or by increasing the efficiency of translation through codon optimization, all methods known to one of skill in the art.

It is envisioned that in addition to the particular strains that were used, any strain of *S. cerevisiae* or *P. stipitis* could be used in the practice of the invention. For example, in addition to *P. stipitis* UC7, one could advantageously obtain expression of the polynucleotides of the invention in *P. stipitis* strains having reduced respiration capacity, such as petite mutants or *P. stipitis* Shi21 (NRRL Y-21971). Similarly, one could advantageously obtain expression of the polynucleotides of the invention in a PHO-13 mutant of *S. cerevisiae* expressing *P. stipitis* XYL1, XYL2, and XYL3. Such a strain was developed, as described in the examples, for use in developing yeast strains according to the invention. Yeasts strains may suitably be modified to include exogenous sequences expressing Xut1 and Sut4 on the same or different nucleic acid. The yeast strains may be modified to include additional advantageous features, as would be appreciated by one skilled in the art.

In addition to *S. cerevisiae* and *P. stepitis*, it is envisioned that other yeast species could be used to obtain yeast strains according to the invention for use in the methods of the invention. Other suitable yeast species include, without limitation, *Candida boidinii, Enteroramus dimorphus, Candida jeffriesii, Debaryomyces hansenii, Candida Guillermondii, Candida shehatae, Brettanomyces naardensis, Candida guillermondii, Candida lyxosophilia, Candida intermedia, Candida tenuis, Hansenula polymorpha, Kluyveromyces marxianus, Kluyveromyces lactis, Kluyveromyces fragilis, Kluyveromyces thermotolerans, Pachysolen tannophilus, Pichia segobiensis, Spathaspora passalidarum* and Pass 1 isolates.

In another aspect, the present invention provides a method of fermenting xylose in a xylose-containing material to produce ethanol using the yeast of the invention as a biocatalyst. Another aspect of the present invention provides a method of fermenting xylose in a xylose-containing material to produce xylitol using the yeast of the invention as a biocatalyst. In this embodiment, the yeast preferably has reduced xylitol dehydrogenase activity such that xylitol is accumulated. Preferably, the yeast is recovered after the xylose in the medium is fermented to ethanol and used in subsequent fermentations.

The constructs of the invention comprise a coding sequence operably connected to a promoter. Preferably, the promoter is a constitutive promoter functional in yeast, or an inducible promoter that is induced under conditions favorable to uptake of sugars or to permit fermentation. Inducible promoters may include, for example, a promoter that is enhanced in response to particular sugars, or in response to oxygen limited conditions, such as the FAS2 promoter used in the examples. Examples of other suitable promoters include promoters associated with genes encoding *P. stipitis* proteins which are induced in response to xylose under oxygen limiting conditions, including, but not limited to, myo-inositol 2-dehydrogenase (MOR1), aminotransferase (YOD1), guanine deaminase (GAH1). These proteins correspond to protein identification numbers 64256, 35479, and 36448 on the Joint Genome Institute *Pichia stipitis* web site: genome.jgi-psf.org/Picst3/Picst3.home.html.

Oxygen limiting conditions include conditions that favor fermentation. Such conditions, which are neither strictly anaerobic nor fully aerobic, can be achieved, for example, by growing liquid cultures with reduced aeration, i.e., by reducing shaking, by increasing the ratio of the culture volume to flask volume, by inoculating a culture medium with a number of yeast effective to provide a sufficiently concentrated initial culture to reduce oxygen availability, e.g., to provide an initial cell density of 1.0 g/l dry wt of cells.

By "xylose-containing material," it is meant any medium comprising xylose, whether liquid or solid. Suitable xylose-containing materials include, but are not limited to, hydrolysates of polysaccharide or lignocellulosic biomass such as corn hulls, wood, paper, agricultural by-products, and the like.

By a "hydrolysate" as used herein, it is meant a polysaccharide that has been depolymerized through the addition of water to form mono and oligosaccharides. Hydrolysates may be produced by enzymatic or acid hydrolysis of the polysaccharide-containing material, by a combination of enzymatic and acid hydrolysis, or by an other suitable means.

Preferably, the yeast strain is able to grow under conditions similar to those found in industrial sources of xylose. The method of the present invention would be most economical when the xylose-containing material can be inoculated with the mutant yeast without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. Serially subculturing yeast selects for strains that are better able to grow in the presence of sulfite or phenolic inhibitors.

It is expected that yeast strains of the present invention may be further manipulated to achieve other desirable characteristics, or even higher specific ethanol yields. For example, selection of mutant yeast strains by serially cultivating the mutant yeast strains of the present invention on medium containing hydrolysate may result in improved yeast with enhanced fermentation rates.

The following non limiting examples are intended to be purely illustrative.

EXAMPLES

Characterization of Putative Xylose Transporters of *Pichia stipitis*

Yeast strains, plasmids, and growth conditions. The yeast strains and the plasmids used in this study are listed in Table 1. *S. cerevisiae* EBY.VW4000 strain (MATa Δhxt1-17 Δgal2 Δstl1 Δagt1 Δmph2 Δmph3 leu2-3,112 ura3-52 trp1-289 his3-Δ1 MAL2-8c SUC2) (9) was kindly provided by E. Boles at Heinrich-Heine-Universitat and was used for transformation of all the constructed plasmids. Three xylose transporter candidates, XUT1, XUT1 partial (corresponding to the sequence encoding the C-terminal region of the protein beginning with amino acid residue 154 of SEQ ID NO:2), and SUT4, were amplified and fused with the TDH3 promoter by PCR. The coding sequence of SUT4 includes a CUG codon, which in *P. stipitis*, specifies the serine residue of amino residue 410 of SEQ ID NO:4. This codon, which in most organisms specifies a leucine, was modified for expression in *S. cerevisiae* using standard methods so as to specify a serine residue. Each candidate had its own terminator. These fragments were then inserted into pRS316 after sequence confirmation (Sikorski & Hieter (1989) Genetics 122, 19-27). Genetic manipulation and cloning of DNA were performed using methods known in the art. *Escherichia coli* DH5αF' was used as a host for plasmid preparation.

Yeast transformation was performed as previously described (Gietz & Woods (2002) Methods Enzymol 350, 87-96). Yeast transformants were selected by TRP1 and URA3 selectable markers and cultivated on yeast synthetic complete dropout (TRP− URA−) medium with carbon source (Kaiser et al. & Cold Spring Harbor Laboratory. (1994) Methods in yeast genetics: a Cold Spring Harbor Laboratory course manual (Cold Spring Harbor Laboratory Press, Cold Spring Harbor, N.Y.)). Yeast cells were cultured in a 125-ml flask with 50 ml medium at 30° C. and 200 rpm.

Quantitative PCR (qPCR) Total RNA was prepared from each transformant and 5 μg of total RNA was used for cDNA construction with random oligonucleotides and the Reverse Transcription System Kit (Promega, Madison, Wis.). Reverse Transcription-PCR primers were designed using Primer Express software (Applied Biosystems). RT-PCR was performed with SYBR green PCR master mix (Applied Biosystems) and an ABI PRISM 7000 sequence detection system (Applied Biosystems). PCR conditions were as recommended by the manufacturer except that one-half of the reaction volume was used. Actin was used to normalize the relative copy numbers of each gene. All reactions were performed in triplicate.

TABLE 1

List of yeast strains and plasmids

| Strain or plasmid | Description | Source or reference |
|---|---|---|
| Strains | | |
| *S. cerevisiae* EBY.VW4000 | MATa Δhxt1-17 Δgal2 Δstl1 Δagt1 Δmph2 Δmph3 leu2-3,112 ura3-52 trp1-289 his3-Δ1 MAL2-8$^c$ SUC2 | Wieczorke |
| *S. cerevisiae* JYB3005 | *S. cerevisiae* EBY.VW4000(pRS314 and pRS316) | This study |
| *S. cerevisiae* JYB3011 | *S. cerevisiae* EBY.VW4000(pRS314-X123 and pRS316) | This study |
| *S. cerevisiae* JYB3110 | *S. cerevisiae* EBY.VW4000(pRS314-X123 and pRS316-XUT1partial) | This study |
| *S. cerevisiae* JYB3210 | *S. cerevisiae* EBY.VW4000(pRS314-X123 and pRS316-XUT1) | This study |
| *S. cerevisiae* JYB3310 | *S. cerevisiae* EBY.VW4000(pRS314-X123 and pRS316-SUT4) | This study |
| Plasmids | | |
| pRS314 | TRP1 CEN/ARS | Sikorski |
| pRS316 | URA3 CEN/ARS | Sikorski |
| pRS314-X123 | TRP1 CEN/ARS TDH3$_P$-PsXYL1-TDH3$_T$ TDH3$_P$-PsXYL2-TDH3$_T$ TDH3$_P$-PsXYL3-TDH3$_T$ | Ni |
| pRS316-XUT1partial | URA3 CEN/ARS TDH3$_P$-PsXUT1 | This study |
| pRS316-XUT1 | URA3 CEN/ARS TDH3$_P$-PsXUT1 | This study |
| pRS316-SUT4 | URA3 CEN/ARS TDH3$_P$-PsSUT4 | This study |

Sugar-transport assay. Initial D-[14C]xylose and D-[$^{14}$C] glucose (Amersham) uptake rates were measured at 30° C., pH 5.0 as previously described (Spencer-Martins, I. a. c. U., N. (1985) Biochim. Biophys. Acta 812, 168-172). Cells were harvested in the mid-exponential phase (A$_{600}$nm 0.8-1.0; ≈0.1-0.125 g/l dry wt) by centrifugation, washed twice with ice-cold water and resuspended to a cell concentration of 5-10 mg (dry weight)/ml. Kinetic parameters were determined using Lineweaver-Burk plots. All measurements were conducted at least three times, and the data reported are the average values.

Transcriptional analysis of eight xylose transporter candidates. Eight putative xylose transporters (XUT1-7 and SUT4) were identified based on genomic analysis of the genome sequence of *Pichia stipitis* (Jeffries et al. (2007) Nat Biotechnol 25, 319-26) and selected for further analysis. Of these eight putative transporters, XUT1, and SUT4 showed increased expression in *Pichia stipitis* grown in xylose-containing media. These two genes were introduced into the host strain *S. cerevisiae* JYB3011 to evaluate the ability of the putative xylose transporters to promote xylose uptake. This host strain was originated from *S. cerevisiae* EBY.VW4000 (Wieczorke et al. (1999) FEBS Lett 464, 123-8) and engineered to express PsXYL1, PsXYL2, and PsXYL3 by introducing pRS314-X123 (Ni et al. (2007) Appl Environ Microbiol 73, 2061-6) (Table 1).

Kinetic characteristics of sugar uptake. XUT1 partial, XUT1 and SUT4 were expressed in the strains *S. cerevisiae*

Figure 3:
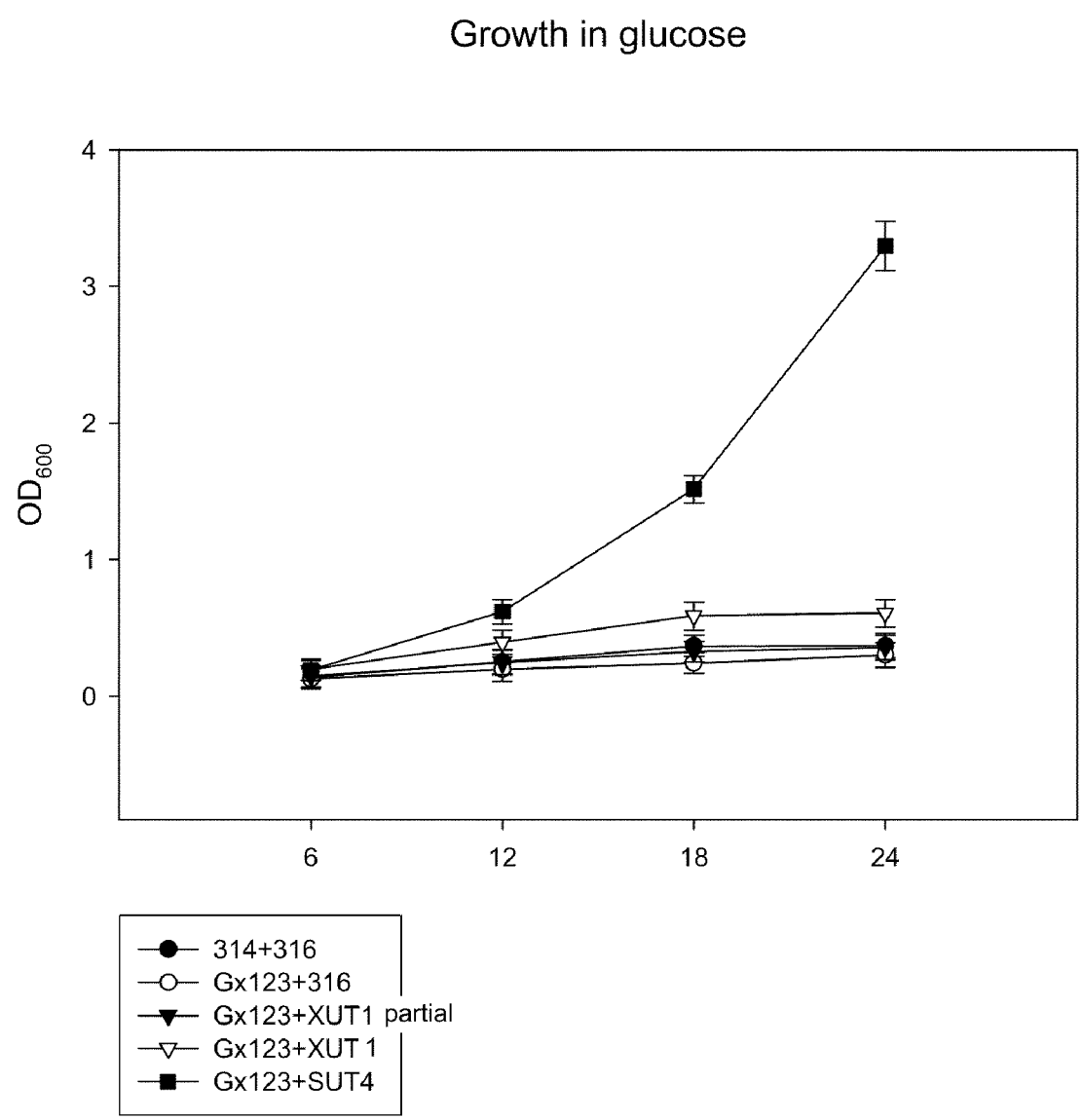
FIG. 3 shows growth, measured as $OD_{600}$, of *S. cerevisiae* expressing XUT1 or SUT4 on glucose as a function of time.
Figure 4:
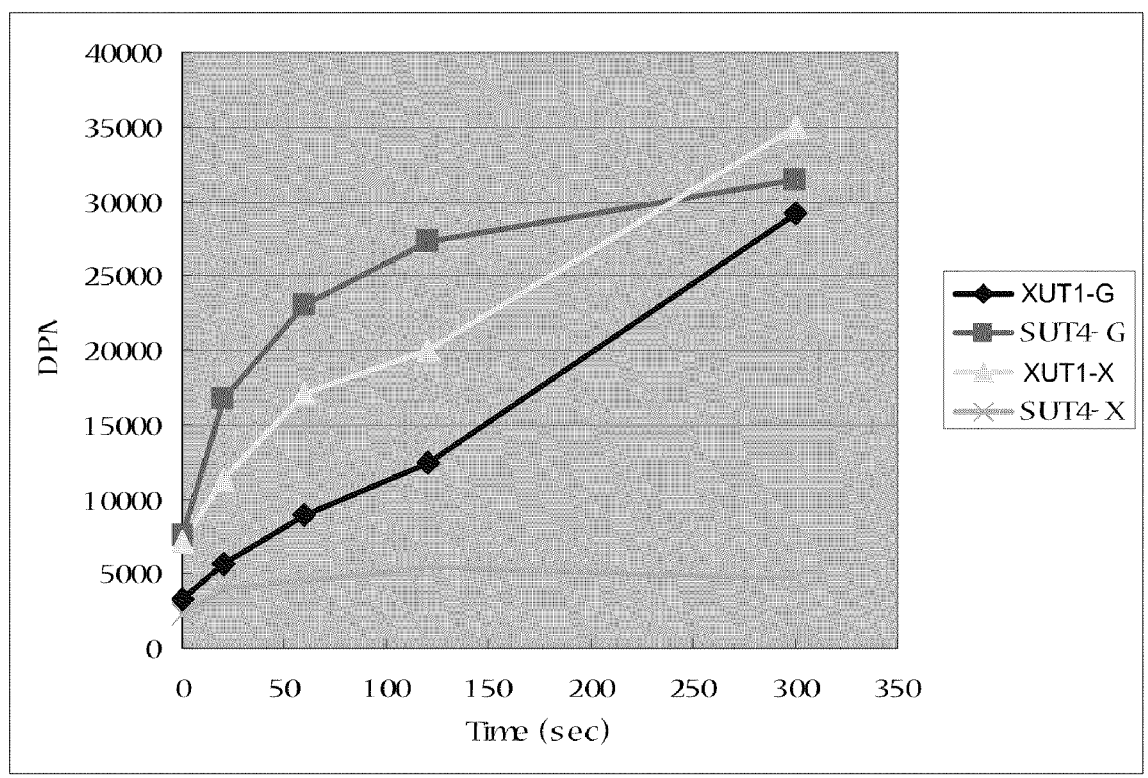
FIG. 4 shows uptake of $^{14}C$-glucose or $^{14}C$-xylose, measured as DPM, by *S. cerevisiae* expressing XUT1 or SUT4 as a function of time.

JYB3110, JYB 3210, and JYB3310, respectively (Table 1). The expression of each transporter in its respective strain was confirmed by qPCR (data not shown). These three strains could grow in xylose-containing media (FIG. 2) and in glucose-containing media (FIG. 3). Xylose and glucose transport capacity of each candidate was tested using a high concentration (50 mM) of labeled sugar (Table 2). The strains containing Xut1 or Sut4 showed increased xylose uptake activities, with the strain expressing Xut1 having a higher uptake rate than that of the strain expressing Sut4 (FIG. 4). Both JYB 3210 and JYB3310 showed glucose-transporting activity, with Sut4 conferring a higher glucose uptake velocity than Xut1 (FIG. 4).

Kinetic analysis demonstrated that the affinity of Xut1 for xylose is 3-fold higher than its affinity for glucose (FIG. 4 and Table 3). This is the first reported transporter having a higher affinity for xylose. Vmax was also higher with xylose than glucose. Although Sut4 exhibits xylose uptake activity, its affinity for glucose is 12 times higher than its affinity for xylose (Table 3). Interestingly, Sut4 has higher Vmax with xylose than glucose. Notably, Sut4 has a higher specificity ratio (Vmax/Km) for both xylose and glucose than any of the other four glucose/xylose facilitators found in *Pichia stipitis* (Table 3).

Table 3 compares Km values of the newly discovered xylose transporters to previously characterized xylose transporters. All four of the PsSut glucose/xylose facilitators show similar affinities for glucose, but their affinities for xylose differ significantly. Notably, PsSut4 shows a higher specificity ratio (Vmax/Km) for glucose and xylose than the specificity ratios of PsSut1-3. Interestingly, PsSut1 has about 78% amino acid identity with PsSut2, 3 and 4, whereas PsSut2 and PsSut4 differ from PsSut3 by one or two amino acids each (Sut2: L279V; Sut4: L279V, A544T). Despite the high degree of sequence identity, PsSut1-4 have distinct properties. PsSut1 and PsSut3 can mediate fructose transport, whereas PsSut2 cannot, and only PsSut3 can mediate galactose transport (Weierstall et al. (1999) Molecular Microbiol. 31:871-883). Notably, among PsSut1-4, PsSut4 has the highest affinity and the second highest Vmax for xylose. The affinity of PsSut4 for xylose is about three times higher than that of PsSut2, and its Vmax for xylose uptake is about 4.4 times higher than the Vmax of Sut2.

Energy requirements for sugar transport were evaluated by including the metabolic uncoupler sodium azide. Xut1 mediated uptake of sugar was reduced by 96% in the presence of sodium azide, whereas Sut4 mediated sugar uptake was reduced by about 50% (Table 4). Consequently, Xut1 is believed to be a high affinity xylose-proton symporter, and SUT4 appears to employ facilitated diffusion.

TABLE 2

Initial uptake rates of labeled sugar (50 mM) of each putative xylose transporter.

| Strain | Substrate | V[‡] |
|---|---|---|
| JYB3011 (Control) | Glucose | 5 |
|  | Xylose | 0 |
| JYB3110 (XUT1 partial) | Glucose | 7 |
|  | Xylose | 0 |
| JYB3210 (XUT1) | Glucose | 31.8 |
|  | Xylose | 57.8 |
| JYB3310 (SUT4) | Glucose | 52.6 |
|  | Xylose | 23.1 |

[‡]Velocity of uptake (milimoles per minutes per milligram [dry weight])

TABLE 3

Kinetic parameters of yeast glucose/xylose transporters

| Transporters | $K_m$ (mM) | | $V_{max}$ (nmol min$^{-1}$ mg dw$^{-1}$) | | Specificity $V_{max}/K_m$ | | Reference |
|---|---|---|---|---|---|---|---|
|  | Glucose | Xylose | Glucose | Xylose | Glucose | Xylose |  |
| PsSut1 | 1.5 ± 0.1 | 145.0 ± 1.0 | 45 ± 1.0 | 132 ± 1.0 | 30.0 | 0.9 | (4) |
| PsSut3 | 0.8 ± 0.1 | 103 ± 3.0 | 3.7 ± 0.2 | 87 ± 2.0 | 4.6 | 0.8 | (4) |
| PsSut2 | 1.1 ± 0.1 | 49.0 ± 1.0 | 3.3 ± 0.1 | 28 ± 4.0 | 3.3 | 0.6 | (4) |
| PsSut4 | 1.3 ± 0.1 | 16.6 ± 0.3 | 105 ± 4.2 | 122 ± 2.4 | 80.8 | 7.4 | This study |
| CiGxf1 | 2.0 ± 0.6 | 48.7 ± 6.5 | ≈163[†] | ≈25[†] | 81.5 | 0.5 | (1) |
| ScHxt1 | [a]107 ± 49 | [b]880 ± 8 | [a]50.9 ± 3.7 | [b]750 ± 94 | 0.5 | 0.8 | [a](2) [b](3) |
| ScHxt2 | [a]2.9 ± 0.3 | [b]260 ± 130 | [a]15.6 ± 0.9 | [b]340 ± 10 | 5.4 | 1.3 | [a](2) [b](3) |
| ScHxt4 | [a]6.2 ± 0.5 | [b]170 ± 120 | [a]12.0 ± 0.9 | [b]190 ± 23 | 1.9 | 1.1 | [a](2) [b](3) |
| ScHxt7 | [a]1.3 ± 0.3 | [b]130 ± 9 | [a]11.7 ± 0.3 | [b]110 ± 7 | 90.0 | 0.8 | [a](2) [b](3) |
| CiGxs1 | 0.012 ± 0.004 | 0.4 ± 0.1 | 4.3 ± .33 | 6.5 ± 1.5 | 358.3 | 16.2 | (1) |
| PsXut1 | 0.91 ± 0.01 | 0.46 ± 0.02 | 80 ± 1.0 | 116 ± 5.8 | 87.91 | 252.2 | This study |

[†]Calculated from FIG. 2 of (1)

1. Leandro, M. J., P. GonÁalves, and I. Spencer-Martins. 2006. Two glucose/xylose transporter genes from the yeast *Candida* intermedia: first molecular characterization of a yeast xylose-H+ symporter. The Biochemical journal 395: 543-549.
2. Maier, A., B. Volker, E. Boles, and G. F. Fuhrmann. 2002. Characterisation of glucose transport in *Saccharomyces cerevisiae* with plasma membrane vesicles (countertransport) and intact cells (initial uptake) with single Hxt1, Hxt2, Hxt3, Hxt4, Hxt6, Hxt7 or Gal2 transporters. Fems Yeast Research 2: 539-550.
3. Saloheimo, A., J. Rauta, O. V. Stasyk, A. A. Sibirny, M. Penttila, and L. Ruohonen. 2007. Xylose transport studies with xylose-utilizing *Saccharomyces cerevisiae* strains expressing heterologous and homologous permeases. Applied Microbiology And Biotechnology 74: 1041-1052.
4. Weierstall, T., C. P. Hollenberg, and E. Boles. 1999. Cloning and characterization of three genes (SUT1-3) encoding glucose transporters of the yeast *Pichia stipitis*. Molecular Microbiology 31: 871-883.

TABLE 4

Effect of sodium azide on glucose and xylose uptake[‡].

|  | Glucose | | Xylose | |
|---|---|---|---|---|
|  | Control | NaN$_3$ (50 mM) | Control | NaN$_3$ (50 mM) |
| JYB3110 (SUT4) | 41 | 0.32 | 90 | 3.19 |
| JYB3310 (XUT1) | 40 | 25 | 13.4 | 9.2 |

[‡]Velocity of uptake (nmol min$^{-1}$ mg$^{-1}$ [dry weight])

Effect of Expression of Sut4 in *P. stipitis*

Construction of plasmids and transformation of yeast strains. A plasmid was constructed to contain the *P. stipitis* coding sequence for the SUT4 putative transporter under the control of the *P. stipitis* fatty acid synthase subunit alpha (Fas2) promoter (FAS2p_SUT4_SUT4t_LoxP_URA3_LoxP plasmid). Roughly 100 ug of the FAS2p_SUT4_SUT4t_LoxP_Ura3_LoxP plasmid was linearized using Hind III and ApaI, ethanol precipitated and resuspended in water to create a fragment that would integrate directly into the *Pichia* genome. The digested construct was then used in a LiAc protocol and transformed into either the yJML123 (Gietz & Woods (2002) Methods Enzymol 350, 87-96)) or UC7 *Pichia stipitis* strains. The yJML123 strain has a deletion in the XYL2 gene, which encodes the enzyme that catalyzes the conversion of xylitol to xylulose, allowing us to create *Pichia* strains that will begin to accumulate xylitol.

Transformants were selected for via growth on ScD –Ura plates, which contain 0.62 g/L CSM –Leu –Trp –Ura (Bio 101 Systems) and dextrose (2%). Colonies were then picked and grown overnight in ScD –Ura liquid media. Genomic DNA was then extracted and evaluated by PCR to confirm integration of the construct. As a control for these strains, a plasmid containing only the LoxP_Ura3_LoxP cassette was also integrated into the yJML123 and UC7 strains (yJML123 and UC7 controls).

Fermentation of yJML123+SUT4 Starter cultures were established by inoculating a single colony of yJML123+SUT4 strain or yJML123 control from recently streaked plate into 25 mL fermentation media and grown overnight. The following morning, triplicate flask cultures of each transformant were started at an $OD_{600}$ of 0.5 (≈0.06 g/l dry wt of cells). The transformants were confirmed using PCR genotyping. The fermentation was run under aerobic conditions using an agitation speed of 200 rpm at 30° C. in 25 mL of media in a 125 mL flask in fermentation medium (Yeast Nitrogen Base (1.7 g/L), urea (2.4 g/L), peptone (3.6 g/L), with xylose (40 g/L) and glucose (17 g/L) as carbon sources. Samples were collected for analysis roughly every 8 hours for the first 48 hours and then once every 24 hours.

The yJML123+SUT4 strain was able to use both glucose and xylose at a faster rate than the control strain. Neither strain was able to use all of the xylose. The yJML123+SUT4 strain produced a higher yield of xylitol (18.45 g/L) than the control strain (15.51 g/L). Further, the yJML123+SUT4 strain produced a higher yield of xylitol faster than the control.

Fermentation of UC7+SUT4. Starter cultures were established by inoculating a single colony of SUT4+UC7 strain or the UC7 control from recently streaked plates into 50 mL of fermentation media and grown overnight. The following morning, triplicate flasks of each transformant were started at an $OD_{600}$ of 0.5 (≈0.06 g/l dry wt of cells). The transformants were confirmed using PCR genotyping. The fermentation was run in fermentation medium (Yeast Nitrogen Base (1.7 g/L), urea (2.4 g/L), peptone (3.6 g/L), and xylose (40 g/L), under low oxygen conditions using an agitation speed of 100 rpm at 30° C. in 50 mL of media in a 125 mL flask. The starting $OD_{600}$ was 10 (≈1.25 g/l dry wt of cells). Samples were collected for analysis roughly every 12 hours for the first 60 hours and then once every 24 hours.

Fermentation of UC7+SUT4. The UC7+SUT4 strain was found to use xylose at a faster rate than the UC7 control; neither strain used all of the xylose. The xylitol yield of UC7+SUT4 strain was similar to that of the UC7 control. The UC7+SUT4 strain had a higher ethanol specific productivity than that of the UC7 control.

Evaluation of Expression of SUT4 in *P. stipitis* in Bioreactor

Strain Descriptions. The UC7+SUT4 strain described above ("SUT4") and the UC7+URA3 cassette strain ("control") described above were evaluated in a three liter bioreactor scale-up as described below.

3 L Bioreactor Scale-up of the SUT4 Transporter Overexpression Strain. Low oxygen bioreactor trials were used to compare two strains in a larger scale and under more controlled conditions than shake flask trials.

Bioreactor Cultivations. A defined minimal medium containing trace metal elements and vitamins was used in all bioreactor cultivations. This medium was modified based on that described by Verduyn et al. (Verduyn et al. (1992) Yeast 8:501-517) to include urea as a nitrogen source. It had the following composition: 2.4 g urea $L^{-1}$; 3 g $KH_2PO_4$ $L^{-1}$, 0.5 g $MgSO_4$ $7H_2O$ $L^{-1}$; 1 ml trace element solution $L^{-1}$; 1 ml vitamin solution $L^{-1}$; and 0.05 ml antifoam 289 (Sigma A-8436) $L^{-1}$ (Jeffries & Jin (2000) Adv Appl Microbiol 47, 221-68). For these cultivations, a starting concentration of 70 g $L^{-1}$ glucose and 30 g $L^{-1}$ xylose was used.

Cultivations were performed in 3 L New Brunswick Scientific BioFlo 110 Bioreactors with working volumes of 2 liters. All cultivations were performed at 30° C. Agitation was set at 500 rpm and the pH was controlled at pH 5.0 by the addition of 5 N KOH and 5 $NH_2SO_4$. Aeration was controlled at a rate of 0.5 vvm which corresponded to a rate of 1 L $min^{-1}$. Input gas was mixed using a gas proportioner to include 90% pure nitrogen and 10% air, for a final oxygen concentration of approximately 2%. Bioreactors were inoculated to an OD of approximately 1 and their progress followed for 74 hours.

During cultivation, the SUT4 strain appeared to grow faster than the control. Calculated biomass rates and yields demonstrated that SUT4 had a slightly improved growth rate (~1.2 fold) (0.062 vs. 0.0514 $h^{-1}$) and biomass yield (0.151 g dry cell weight/g glucose vs. 0.145 g dry cell weight/g glucose, or 0.184 Cmmol vs. 0.177 Cmmol). As was observed previously in the shake flask experiments described above, the overall difference in ethanol yield from glucose was not large. The SUT4 strain had a slightly higher (~1.11 fold) ethanol yield on glucose (0.372 g ethanol/g glucose or 0.485 Cmmol) than the control strain (0.335 g ethanol/g glucose or 0.437 Cmmol/Cmmol glucose).

Figure 5:
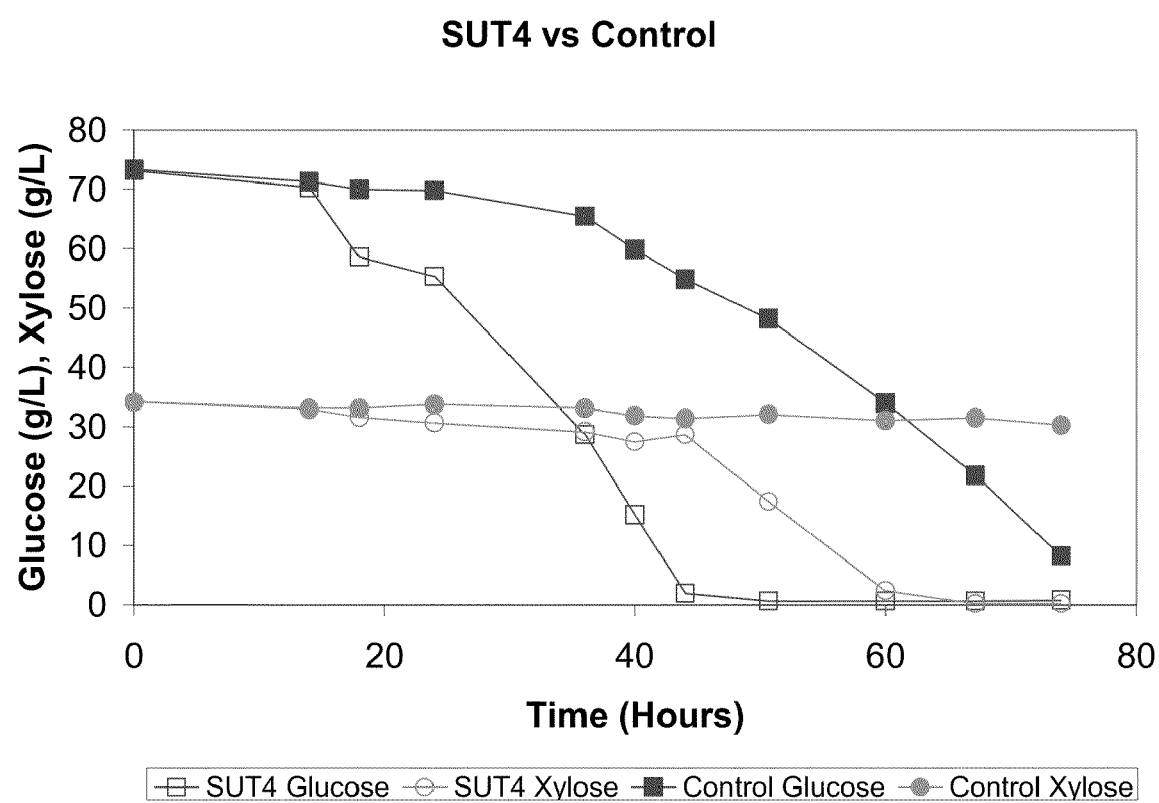
FIG. 5 shows consumption of glucose and xylose by *Pichia stipitis* overexpressing SUT 4 as a function of time.

The major difference between these two strains is in their kinetic rates of glucose and xylose consumption. The SUT4 strain consumes glucose at a much higher rate than the control strain (FIG. 5). In fact, the SUT4 strain consumed all of the glucose and xylose in the fermentation, while the URA3 control strain consumed approximately 88% of the glucose and did not consume enough xylose to significantly change the xylose concentration during the length of the fermentation.

The specific rate of glucose consumption for the SUT4 strain (0.284 g glucose $gDCW^{-1}h^{-1}$ or 9.448 Cmmol $gDCW^{-1}h^{-1}$) was 3.04 fold higher than that of the URA3 control strain (0.093 g Glucose $gDCW^{-1}h^{-1}$ or 3.106 Cmmol $gDCW^{-1}h^{-1}$). The specific rates of xylose consumption could not be compared due to the fact that the URA3 control strain had not significantly begun to utilize the xylose. Further bioreactor trials will be necessary to compare these rates.

Figure 6:
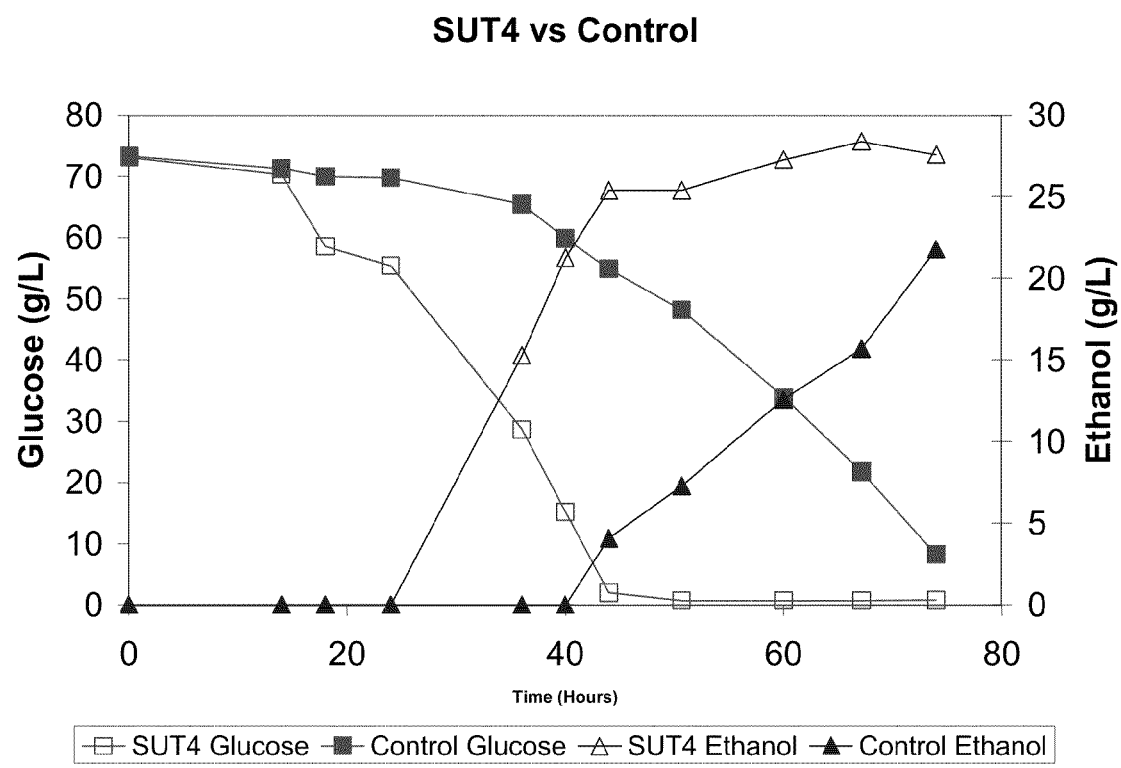
FIG. 6 shows glucose consumption and ethanol production by *Pichia stipitis* overexpressing SUT4 as a function of time.

The SUT4 and control strains also exhibited different rates of ethanol production. FIG. 6. shows a plot of ethanol production and glucose consumption. It should be noted that a small amount of ethanol produced by the SUT4 overexpression strain was due to the xylose consumed; however the rates and yields were calculated using the glucose only phase of fermentation. The specific rate of ethanol production for the SUT4 overexpression strain (0.106 g ethanol $gDCW^{-1}h^{-1}$ or 4.580 Cmmol gDCW$^{-1}$h$^{-1}$) was 3.38 fold higher than that of the control strain (0.031 g ETOH gDCW$^{-1}$h$^{-1}$ or 1.356 Cmmol gDCW$^{-1}$h$^{-1}$).

Creation of the Δpho13 Background Strains for Transporter Testing

In order to test the effect of putative transporters on xylose utilization, a robust *Saccharomyces cerevisiae* background that is capable of utilizing xylose in some capacity needed to be built. Previous research has shown that either the overexpression of TAL1 or the deletion of PHO13 promotes growth on xylose when the *Pichia stipitis* xylulokinase gene is expressed at a high level (10). The PHO13 deletion was chosen for use in these strains, as more detailed kinetic data during aerobic and low oxygen cultivations is available for a strain created in a similar genetic background (Van Vleet et al. (2008) Metab. Eng. Doi10.1016/j.ymben.2007.12.002).

The strains CEN.PK.111-27B and CEN.PK.102-3A were chosen as the genetic backgrounds in which to create these deletion strains (Entian K, Kotter P, (2007) 25 Yeast Genetic Strain and Plasmid Collections. In: Methods in Microbiology; Yeast Gene Analysis—Second Edition, Vol. Volume 36 (Ian Stansfield and Michael J R Stark ed), pp 629-666. Academic Press). The CEN.PK.111-27B carries the trp1 and leu2 mutations and the CEN.PK.102-3A strain carries the ura3 and leu2 mutations. The deletion of the PHO13 in these backgrounds will allow for the putative transporters to be tested in the presence of the xylose utilization genes expressed moderately and, separately, at a high level. These transporters will also be able to be tested at 2 different levels of expression. Moderate expression of the transporters will be possible using a centromeric LEU2 plasmid and high levels of expression will be possible using a multicopy LEU2 plasmid with a 2 μm origin of replication.

The PHO13 deletion cassette was amplified out of the genomic DNA of *S. cerevisiae* CMB.JHV.pho13a (Van Vleet et al. (2008) Metab. Eng. Doi10.1016/j.ymben.2007.12.002) using the high fidelity Pfusion polymerase (NEB, Finnzymes) and primers designed 400 bp upstream and downstream of the PHO13 open reading frame. This cassette contains the KANMX gene and has been shown previously to confer G418 resistance to PHO13 knockout strains in *S. cerevisiae* (Van Vleet et al. (2008) Metab. Eng. Doi10.1016/j.ymben.2007.12.002).

HpaI sites were added onto the ends of this amplified fragment for easy excision from a storage vector. The primers used in strain creation and confirmation are listed in Table 5. The amplified fragment was ligated into the pCR4Blunt-TOPO vector and then transformed into TOP10 *E. coli* by a heat shock method. Transformants were selected for on kanamycin plates and digest checked to confirm the size of the insert. After verification, 100 μg of plasmid DNA was prepared using a Qiagen maxiprep and digested with HpaI to release the deletion cassette. The deletion cassette was then gel purified.

The purified deletion cassette was then transformed into the CEN.PK strains using a standard lithium acetate method (Gietz & Woods (2002) Methods Enzymol 350, 87-96)). Outgrowth was performed after the transformation for 3 hours in YPD liquid media, and then transformants were selected for on YPD plates containing 250 mg/ml G418. After 2 days of growth, growth of putative knockouts was confirmed by re-streaking on fresh G418 plates. These strains were then genotyped using primers that were designed 600 bp upstream and downstream of the PHO13 open reading frame. These primers amplify a product in both deletion and non deletion strains, however in deletion strains the product is approximately 650 bp larger than in the non deletion strain. Multiple transformants for each strain were identified as containing the deletion. Transformants containing the deletion originating from CEN.PK.111-27B were designated FPL.JHV.002 and those originating from CEN.PK.102-3A were designated FPL.JHV.003.

The xylose utilization genes (XYL1, XYL2, and XYL3) under the control of the strong constitutive TDH3 promoter were then introduced to the strains via plasmid. FPL.JHV.002 was transformed with the centromeric vector pRS314-X123 (10) and designated FPL.JHV.004. At the same time, FPL.JHV.003 was transformed with the multicopy vector pYES2-X123 (10) and designated FPL.JHV.005. Both of the vector bearing strains carry a leu2 marker to allow for testing of the putative transporters. The plasmids and yeast strains are described in Table 6.

TABLE 5

Primers Used

| Primer Name | Function | Sequence |
|---|---|---|
| oFPL.JHV.021 | PHO13F + HpaI | GATTACATGTTAACGATTGTTCGACGCAACTACCC (SEQ ID NO: 8) |
| oFPL.JHV.022 | PHO13R + HpaI | GATTACATGTTAACCTTCCCCAACAAGACCGAATTG (SEQ ID NO: 9) |
| oFPL.JHV.023 | PHO13 Confirmation F | TTAAAACAAGAATTTGGGGAG (SEQ ID NO: 10) |
| oFPL.JHV.024 | PHO13 Confirmation | AAAGGTCTAATTATTCAATTTATCGAC (SEQ ID NO: 11) |

Assessment of putative transporters by whole genome expression array technology. Cells of *Pichia stipitis* were cultivated in a bioreactor with either xylose or glucose as carbon sources along with mineral nutrients and urea for a nitrogen source using the medium of Verduyn et al. (16). Cells were grown either under fully aerobic or oxygen limited conditions. Cells were harvested, their mRNA was extracted and analyzed using a whole-genome expression array (NimbleGen). Transcripts corresponding to putative sugar transporters were identified and annotated. (Results not shown). Transcripts for seven genes (HXT2.4, HXT4, SUC1.5, XUT1, SUT4, XUT7 and YBR2) were induced to a higher level in cells grown on xylose than in cells grown on glucose. All but SUT4 were induced to their highest levels on xylose under oxygen limiting conditions. Transcripts for seven genes (AUT1, HGT2, HUT1, AML4, RGT2, STL1 and SUT1) were all induced to their highest levels when cells were cultivated on glucose. Transcript for one gene (SUT1) was induced to its highest level under oxygen limitation; the other six were induced to their highest levels under aerobic conditions. The specific induction of transcripts on xylose under aerobic or oxygen limited conditions was taken as an indicator of the effective function of this gene when cells were cultivated on xylose. Of these genes, SUT1, SUT2 and SUT3 were previously recognized and described as glucose/xylose facilitator transport proteins.

It is to be understood that the invention is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

We claim:

1. A nucleic acid construct comprising a coding sequence operably linked to a promoter not natively associated with the coding sequence, the coding sequence encoding a glucose/xylose transporter polypeptide having at least 95% amino acid identity to SEQ ID NO:4, wherein the polypeptide comprises a serine residue at the amino acid position corresponding to position 544 of SEQ ID NO:4.

2. The construct of claim 1, wherein the promoter is a constitutive promoter.

3. The construct of claim 1, wherein the promoter is inducible under oxygen limiting conditions.

4. The construct of claim 1, wherein the polypeptide comprises SEQ ID NO:4.

5. The construct of claim 1, wherein the coding sequence comprises at least one of the sequences shown in FIG. 1.

6. The construct of claim 1, wherein the coding sequence comprises SEQ ID NO:3.

7. A vector comprising the construct of claim 1.

8. A yeast strain comprising the construct of claim 1.

9. The strain of claim 8, wherein the strain exhibits increased uptake of xylose relative to a control yeast lacking the construct.

10. The strain of claim 8, wherein the strain has a higher specific rate of ethanol production relative to a control yeast lacking the construct.

11. The strain of claim 8, wherein the strain exhibits increased xylitol production relative to a control yeast lacking the construct.

12. The strain of claim 11 wherein the strain has reduced xylitol dehydrogenase activity such that xylitol accumulates.

13. The strain of claim 8, wherein the yeast strain is a *Pichia stipitis*.

14. The strain of claim 8, wherein the yeast strain is a *Saccharomyces cerevisiae*.

15. A method of producing ethanol from the fermentation of xylose comprising: culturing the yeast strain of claim 8 in xylose-containing material under suitable conditions for a period of time sufficient to allow fermentation of at least a portion of the xylose to ethanol.

16. The method of claim 15, wherein the xylose-containing material further comprises glucose.

17. A method of producing xylitol from the fermentation of xylose comprising the step of: culturing the yeast strain of claim 9 in xylose-containing material under suitable conditions for a period of time sufficient to allow fermentation of at least a portion of the xylose to xylitol.

18. The construct of claim 2, wherein the constitutive promoter is TDH3.

19. The construct of claim 3, wherein the promoter is selected from the group consisting of FAS2, MOR1, YOD1 and GAH1.

* * * * *

SEQUENCE LISTING

<160> NUMBER OF SEQ ID NOS: 13

<210> SEQ ID NO 1
<211> LENGTH: 1701
<212> TYPE: DNA
<213> ORGANISM: Pichia stipitis

<400> SEQUENCE: 1

```
atgcacggtg gtggtgacgg taacgatatc acagaaatta ttgcagccag acgtctccag      60
atcgctggta agtctggtgt ggctggttta gtcgcaaact caagatcttt cttcatcgca     120
gtctttgcat ctcttggtgg attggtctac ggttacaatc aaggtatgtt cggtcaaatt     180
tccggtatgt actcattctc caaagctatt ggtgttgaaa agattcaaga caatcctact     240
ttgcaaggtt tgttgacttc tattcttgaa cttggtgcct gggttggtgt cttgatgaac     300
ggttacattg ctgatagatt gggtcgtaag aagtcagttg ttgtcggtgt tttcttcttc     360
ttcatcggtg tcattgtaca agctgttgct cgtggtggta actacgacta catcttaggt     420
ggtagatttg tcgtcggtat tggtgtgggt attctttcta tggttgtgcc attgtacaat     480
gctgaagttt ctccaccaga aattcgtggt tctttggttg ctttgcaaca attggctatt     540
actttcggta ttatgatttc ttactggatt acctacggta ccaactacat tggtggtact     600
ggctctggtc aaagtaaagc ttcttggttg gttcctattt gtatccaatt ggttccagct     660
ttgctcttgg tgttggtat cttcttcatg cctgagtctc caagatggtt gatgaacgaa     720
gacagagaag acgaatgttt gtccgttctt tccaacttgc gttccttgag taaggaagat     780
actcttgttc aaatggaatt ccttgaaatg aaggcacaaa agttgttcga aagagaactt     840
tctgcaaagt acttccctca cctccaagac ggttctgcca agagcaactt cttgattggt     900
ttcaaccaat acaagtccat gattactcac tacccaacct tcaagcgtgt tgcagttgcc     960
tgtttaatta tgaccttcca acaatggact ggtgttaact tcatcttgta ctatgctcca    1020
ttcatcttca gttcttagg tttgtctgga aacaccattt ctcttttagc ttctggtgtt    1080
gtcggtatcg tcatgttcct tgctaccatt ccagctgttc tttgggtcga cagacttggt    1140
agaaagccag ttttgatttc cggtgccatt atcatgggta tttgtcactt tgttgtggct    1200
gcaatcttag gtcagttcgg tggtaacttt gtcaaccact ccggtgctgg ttgggttgct    1260
gttgtcttcg tttggatttt cgctatcggt ttcggttact cttggggtcc atgtgcttgg    1320
gtccttgttg ccgaagtctt cccattgggt ttgcgtgcta agggtgtttc tatcggtgcc    1380
tcttctaact ggttgaacaa cttcgctgtc gccatgtcta ccccagattt tgttgctaag    1440
```

```
gctaagttcg gtgcttacat tttcttaggt ttgatgtgta ttttcggtgc cgcatacgtt    1500
caattcttct gtccagaaac taagggtcgt accttggaag aaattgatga acttttcggt    1560
gacacctctg gtacttccaa gatggaaaag gaaatccatg agcaaaagct taaggaagtt    1620
ggtttgcttc aattgctcgg tgaagaaaat gcttctgaat ccgaaaacag caaggctgat    1680
gtctaccacg ttgaaaaata a                                              1701
```

<210> SEQ ID NO 2
<211> LENGTH: 566
<212> TYPE: PRT
<213> ORGANISM: Pichia stipitis

<400> SEQUENCE: 2

```
Met His Gly Gly Gly Asp Gly Asn Asp Ile Thr Glu Ile Ile Ala Ala
1               5                   10                  15

Arg Arg Leu Gln Ile Ala Gly Lys Ser Gly Val Ala Gly Leu Val Ala
            20                  25                  30

Asn Ser Arg Ser Phe Phe Ile Ala Val Phe Ala Ser Leu Gly Gly Leu
        35                  40                  45

Val Tyr Gly Tyr Asn Gln Gly Met Phe Gly Gln Ile Ser Gly Met Tyr
    50                  55                  60

Ser Phe Ser Lys Ala Ile Gly Val Glu Lys Ile Gln Asp Asn Pro Thr
65                  70                  75                  80

Leu Gln Gly Leu Leu Thr Ser Ile Leu Glu Leu Gly Ala Trp Val Gly
                85                  90                  95

Val Leu Met Asn Gly Tyr Ile Ala Asp Arg Leu Gly Arg Lys Lys Ser
            100                 105                 110

Val Val Val Gly Val Phe Phe Phe Ile Gly Val Ile Val Gln Ala
        115                 120                 125

Val Ala Arg Gly Gly Asn Tyr Asp Tyr Ile Leu Gly Gly Arg Phe Val
    130                 135                 140

Val Gly Ile Gly Val Gly Ile Leu Ser Met Val Val Pro Leu Tyr Asn
145                 150                 155                 160

Ala Glu Val Ser Pro Pro Glu Ile Arg Gly Ser Leu Val Ala Leu Gln
                165                 170                 175

Gln Leu Ala Ile Thr Phe Gly Ile Met Ile Ser Tyr Trp Ile Thr Tyr
            180                 185                 190

Gly Thr Asn Tyr Ile Gly Gly Thr Gly Ser Gly Gln Ser Lys Ala Ser
        195                 200                 205

Trp Leu Val Pro Ile Cys Ile Gln Leu Val Pro Ala Leu Leu Leu Gly
    210                 215                 220

Val Gly Ile Phe Phe Met Pro Glu Ser Pro Arg Trp Leu Met Asn Glu
225                 230                 235                 240

Asp Arg Glu Asp Glu Cys Leu Ser Val Leu Ser Asn Leu Arg Ser Leu
                245                 250                 255

Ser Lys Glu Asp Thr Leu Val Gln Met Glu Phe Leu Glu Met Lys Ala
            260                 265                 270

Gln Lys Leu Phe Glu Arg Glu Leu Ser Ala Lys Tyr Phe Pro His Leu
        275                 280                 285

Gln Asp Gly Ser Ala Lys Ser Asn Phe Leu Ile Gly Phe Asn Gln Tyr
    290                 295                 300

Lys Ser Met Ile Thr His Tyr Pro Thr Phe Lys Arg Val Ala Val Ala
305                 310                 315                 320

Cys Leu Ile Met Thr Phe Gln Gln Trp Thr Gly Val Asn Phe Ile Leu
                325                 330                 335
```

```
Tyr Tyr Ala Pro Phe Ile Phe Ser Ser Leu Gly Leu Ser Gly Asn Thr
                340                 345                 350
Ile Ser Leu Leu Ala Ser Gly Val Gly Ile Val Met Phe Leu Ala
            355                 360                 365
Thr Ile Pro Ala Val Leu Trp Val Asp Arg Leu Gly Arg Lys Pro Val
370                 375                 380
Leu Ile Ser Gly Ala Ile Ile Met Gly Ile Cys His Phe Val Ala
385                 390                 395                 400
Ala Ile Leu Gly Gln Phe Gly Gly Asn Phe Val Asn His Ser Gly Ala
                405                 410                 415
Gly Trp Val Ala Val Phe Val Trp Ile Phe Ala Ile Gly Phe Gly
            420                 425                 430
Tyr Ser Trp Gly Pro Cys Ala Trp Val Leu Val Ala Glu Val Phe Pro
            435                 440                 445
Leu Gly Leu Arg Ala Lys Gly Val Ser Ile Gly Ala Ser Ser Asn Trp
            450                 455                 460
Leu Asn Asn Phe Ala Val Ala Met Ser Thr Pro Asp Phe Val Ala Lys
465                 470                 475                 480
Ala Lys Phe Gly Ala Tyr Ile Phe Leu Gly Leu Met Cys Ile Phe Gly
                485                 490                 495
Ala Ala Tyr Val Gln Phe Phe Cys Pro Glu Thr Lys Gly Arg Thr Leu
            500                 505                 510
Glu Glu Ile Asp Glu Leu Phe Gly Asp Thr Ser Gly Thr Ser Lys Met
            515                 520                 525
Glu Lys Glu Ile His Glu Gln Lys Leu Lys Glu Val Gly Leu Leu Gln
            530                 535                 540
Leu Leu Gly Glu Glu Asn Ala Ser Glu Ser Glu Asn Ser Lys Ala Asp
545                 550                 555                 560
Val Tyr His Val Glu Lys
                565

<210> SEQ ID NO 3
<211> LENGTH: 1653
<212> TYPE: DNA
<213> ORGANISM: Pichia stipitis

<400> SEQUENCE: 3
atgtcctcac aagatttacc ctcgggtgct caaaccccaa tcgatggttc ttccatcctc      60
gaagataaag ttgagcaaag ttcgtcctca aatagccaaa gtgatttagc ttctattcca     120
gcaacaggta tcaaagccta tctcttggtt tgtttcttct gcatgttggt tgccttcggt     180
ggcttcgtat tcggtttcga taccggtact atttccggtt tccttaatat gtctgatttc     240
ctttccagat tggtcaaga tggttctgaa ggaaaatatt tgtctgatat cagagtcggt     300
ttgattgttt ccattttaa cattggttgt gcaattggtg gtattttcct ttctaagata     360
ggagatgttt acggtagaag aattggtatc atttcagcta tggttgtcta tgtcgtcggt     420
ataatcatcc agatctcgtc ccaagataag tggtatcaac ttacaattgg acgtggagtt     480
acaggattag ctgttggtac tgtttcggtt ttgtctccaa tgttcattag tgaaagtgct     540
cccaagcatt tgagaggtac tttggtatac tgttaccaat tatgcatcac cttaggtatt     600
ttcattggtt actgtgtcac ttatggaacc aaagatttaa atgattcaag acaatggaga     660
gttcctttgg gttatgtttt cctttgggct attttcttag ttgttggtat gttggctatg     720
ccagaatccc caagattctt gattgaaaag aagagaatcg aagaagccaa gaagtccctt     780
```

-continued

```
gcaagatcca acaagttgtc tccagaagat ccaggtgtct acactgaagt tcaattgatt      840
caagctggta ttgacagaga agctgctgca ggttctgctt cgtggatgga attgattacc      900
ggtaaaccag ctattttcag aagagttatc atgggaatta tcttacagtc tttgcagcaa      960
ttaactggtg tcaactattt cttctactac ggaactacaa tcttccaagc tgttggtttg     1020
caagattcct tccagacttc catcatctta ggtacagtca actttctttc tacatttgtt     1080
ggtatttggg ccattgaaag atttggaaga agacaatgtt tgttagtcgg ttctgctggt     1140
atgttcgttt gtttcatcat ttactctgtc attggtacaa ctcatttgtt cattgatgga     1200
gtagtagata acgacaacac ccgtcaactg tctggtaatg ctatgatctt tatcacttgt     1260
ttgttcatct tcttctttgc ctgtacttgg gctggaggtg ttttacaat catttccgaa      1320 tcatatccat tgagaatcag atccaaggct atgtctattg ccactgccgc taactggatg     1380
tggggtttct tgatttcatt ctgcactcca ttcattgtta acgccatcaa cttcaagttc     1440
ggctttgtgt ttactggttg tttgctcttt tcgttcttct atgtctactt ctttgtcagc     1500
gaaaccaaag gtttgtcgtt ggaagaagtt gatgagttgt acgctgaggg aattgcacca     1560
tggaaatccg gtgcatgggt tcctccttct gcacaacaac aaatgcaaaa ctctacttat     1620
ggtgccgaaa caaaagagca agagcaagtt tag                                  1653
```

```
<210> SEQ ID NO 4
<211> LENGTH: 550
<212> TYPE: PRT
<213> ORGANISM: Pichia stipitis

<400> SEQUENCE: 4
```

```
Met Ser Ser Gln Asp Leu Pro Ser Gly Ala Gln Thr Pro Ile Asp Gly
1               5                   10                  15

Ser Ser Ile Leu Glu Asp Lys Val Glu Gln Ser Ser Ser Asn Ser
            20                  25                  30

Gln Ser Asp Leu Ala Ser Ile Pro Ala Thr Gly Ile Lys Ala Tyr Leu
        35                  40                  45

Leu Val Cys Phe Phe Cys Met Leu Val Ala Phe Gly Gly Phe Val Phe
    50                  55                  60

Gly Phe Asp Thr Gly Thr Ile Ser Gly Phe Leu Asn Met Ser Asp Phe
65                  70                  75                  80

Leu Ser Arg Phe Gly Gln Asp Gly Ser Glu Gly Lys Tyr Leu Ser Asp
                85                  90                  95

Ile Arg Val Gly Leu Ile Val Ser Ile Phe Asn Ile Gly Cys Ala Ile
            100                 105                 110

Gly Gly Ile Phe Leu Ser Lys Ile Gly Asp Val Tyr Gly Arg Arg Ile
        115                 120                 125

Gly Ile Ile Ser Ala Met Val Val Tyr Val Val Gly Ile Ile Ile Gln
    130                 135                 140

Ile Ser Ser Gln Asp Lys Trp Tyr Gln Leu Thr Ile Gly Arg Gly Val
145                 150                 155                 160

Thr Gly Leu Ala Val Gly Thr Val Ser Val Leu Ser Pro Met Phe Ile
                165                 170                 175

Ser Glu Ser Ala Pro Lys His Leu Arg Gly Thr Leu Val Tyr Cys Tyr
            180                 185                 190

Gln Leu Cys Ile Thr Leu Gly Ile Phe Ile Gly Tyr Cys Val Thr Tyr
        195                 200                 205

Gly Thr Lys Asp Leu Asn Asp Ser Arg Gln Trp Arg Val Pro Leu Gly
    210                 215                 220
```

| | | | | | | | | | | | | | | |
|---|---|---|---|---|---|---|---|---|---|---|---|---|---|---|
| Leu | Cys | Phe | Leu | Trp | Ala | Ile | Phe | Leu | Val | Val | Gly | Met | Leu | Ala | Met |
| 225 | | | | 230 | | | | 235 | | | | 240 | | |
| Pro | Glu | Ser | Pro | Arg | Phe | Leu | Ile | Glu | Lys | Lys | Arg | Ile | Glu | Ala |
| | | | 245 | | | | | 250 | | | | | 255 | |
| Lys | Lys | Ser | Leu | Ala | Arg | Ser | Asn | Lys | Leu | Ser | Pro | Glu | Asp | Pro | Gly |
| | 260 | | | | | 265 | | | | 270 | | | | |
| Val | Tyr | Thr | Glu | Val | Gln | Leu | Ile | Gln | Ala | Gly | Ile | Asp | Arg | Glu | Ala |
| 275 | | | | | 280 | | | | | 285 | | | | |
| Ala | Ala | Gly | Ser | Ala | Ser | Trp | Met | Glu | Leu | Ile | Thr | Gly | Lys | Pro | Ala |
| | 290 | | | | | 295 | | | | 300 | | | | |
| Ile | Phe | Arg | Arg | Val | Ile | Met | Gly | Ile | Ile | Leu | Gln | Ser | Leu | Gln | Gln |
| 305 | | | | 310 | | | | 315 | | | | 320 | | |
| Leu | Thr | Gly | Val | Asn | Tyr | Phe | Tyr | Tyr | Gly | Thr | Thr | Ile | Phe | Gln |
| | | | 325 | | | | | 330 | | | | | 335 | |
| Ala | Val | Gly | Leu | Gln | Asp | Ser | Phe | Gln | Thr | Ser | Ile | Ile | Leu | Gly | Thr |
| | 340 | | | | | 345 | | | | 350 | | | | |
| Val | Asn | Phe | Leu | Ser | Thr | Phe | Val | Gly | Ile | Trp | Ala | Ile | Glu | Arg | Phe |
| 355 | | | | | 360 | | | | | 365 | | | | |
| Gly | Arg | Arg | Gln | Cys | Leu | Leu | Val | Gly | Ser | Ala | Gly | Met | Phe | Val | Cys |
| 370 | | | | 375 | | | | 380 | | | | |
| Phe | Ile | Ile | Tyr | Ser | Val | Ile | Gly | Thr | Thr | His | Leu | Phe | Ile | Asp | Gly |
| 385 | | | | 390 | | | | 395 | | | | 400 | | |
| Val | Val | Asp | Asn | Asp | Asn | Thr | Arg | Gln | Ser | Ser | Gly | Asn | Ala | Met | Ile |
| | | 405 | | | | | 410 | | | | | 415 | | |
| Phe | Ile | Thr | Cys | Leu | Phe | Ile | Phe | Phe | Ala | Cys | Thr | Trp | Ala | Gly |
| | | 420 | | | | 425 | | | | | 430 | | | |
| Gly | Val | Phe | Thr | Ile | Ile | Ser | Glu | Ser | Tyr | Pro | Leu | Arg | Ile | Arg | Ser |
| | | 435 | | | | | 440 | | | | | 445 | | |
| Lys | Ala | Met | Ser | Ile | Ala | Thr | Ala | Ala | Asn | Trp | Met | Trp | Gly | Phe | Leu |
| 450 | | | | | 455 | | | | | 460 | | | | |
| Ile | Ser | Phe | Cys | Thr | Pro | Phe | Ile | Val | Asn | Ala | Ile | Asn | Phe | Lys | Phe |
| 465 | | | | 470 | | | | 475 | | | | 480 | | |
| Gly | Phe | Val | Phe | Thr | Gly | Cys | Leu | Leu | Phe | Ser | Phe | Phe | Tyr | Val | Tyr |
| | | | 485 | | | | | 490 | | | | | 495 | |
| Phe | Phe | Val | Ser | Glu | Thr | Lys | Gly | Leu | Ser | Leu | Glu | Glu | Val | Asp | Glu |
| | | | 500 | | | | | 505 | | | | | 510 | |
| Leu | Tyr | Ala | Glu | Gly | Ile | Ala | Pro | Trp | Lys | Ser | Gly | Ala | Trp | Val | Pro |
| | | 515 | | | | | 520 | | | | | 525 | | |
| Pro | Ser | Ala | Gln | Gln | Gln | Met | Gln | Asn | Ser | Thr | Tyr | Gly | Ala | Glu | Thr |
| | 530 | | | | | 535 | | | | | 540 | | | |
| Lys | Glu | Gln | Glu | Gln | Val |
| 545 | | | | 550 | |

<210> SEQ ID NO 5
<211> LENGTH: 1213
<212> TYPE: DNA
<213> ORGANISM: Pichia stipitis

<400> SEQUENCE: 5

```
gttatgggaa accaattggg taccaaaagt gcaaaattta tatatggata caaaagtta      60 tattagaatt actgtttaga tgcgaataga tgttgatcat ttgtaatagt cctagtatga    120
taccaaaagt gaccgtgggt ctatcatgat agggtggaga tgatctttga tattccaaag    180
caaaagtgtt cccttaaacc agtttagact gaaacaaccg aatgtaatca gggtagatga    240
gaaggcatta agctgtggtg tttggctcaa aaagagattc tacacaatat tggactttga    300
```

```
tttgtatatt ggctatacaa gaatatggca ggccatactg atgctgaaaa gaggttgttg      360
aaaaaagtta tgaatataga actgaaaaat ttgaactaat tgggaaatgt ccgggtaaga      420
catggagact gcatagctgg agagggccaa agtataccgg gctcaagagc accagccaag      480
ggggagtgtc ggacagccga tgggtctgct aatgggaagg gattggaagc gagttaagac      540
ggaaaaagaa aacgttttgt tgaaaccact ttggaccaaa catgagaatt ccagagctgt      600
gtcaaatgga agctccagag ttgggtgcaa aatctgagta taatatttgt tgcgaaatcc      660
aaaatgcaga ccttaactat gggctgagca tcttatctat ctacgtatac tcttatatat      720
cggcactata gcaaaacttt actggctgac acatctcggc tgtaacataa atatctgtta      780
aatccgcctc aacaaagtgt tacccaatct cgtgctggcc acctaaattt gagcttttaa      840
ttgtgtgctt ttaactgtgt ggtcttaact gtgtgcccgt ttctcagcct agccaacatt      900
tctcccaaaa attcgtgtgt caaaagcgtg caccgccaaa ttcctcaaca aaagcgcgtg      960
aatgttggga tgggtctggc gctattctgg caaccgcacc cgtgccgcag tacacaacag     1020
cttggctgca acggtgtcga aaattgttgg aacctgctga atcttttttc gggccgcatg     1080
caggctgcag cccaccagat atcaatgctc catatataag tcgatgattt ctacaaatga     1140
acgaattgta tctcttttct tgaactgtag ttctgatttc tcacttctat agtaattcta     1200
atctcctttc acc                                                        1213

<210> SEQ ID NO 6
<211> LENGTH: 1017
<212> TYPE: DNA
<213> ORGANISM: Pichia stipitis

<400> SEQUENCE: 6
atgtcaacgt cgctagttag acatgtcccg ctcgctagat aggctaataa gccattggaa       60
acaatcggcg atggcagcgg gccacctggc taatattagc ccagtttgtg taggcggaag      120
cactcactcc gtgggagccc aaaaaagatt tggtggcacg aaattccgga gtactgtcgg      180
cagggatgga agtttgtgga gaggcagaga ggcggttaca aaagaaagtc gcgacaggaa      240
gaaaacagta gagaaggtaa tggagagctg ataatagtag agaagaaaag caatttcgag      300
atgcaaaagt atggagagag gtaaagaaat agaaatgagt agtagctgta ggtgcaatac      360
aagatggaga tgggcgagat cacggaataa taagaaaaga aatagtgccg ttgagcagag      420
caggttgttc ctgattacag ccaattagat gaacatgacg tttaccggga aatctcgcaa      480
tcgagtgtgc tgatgaacag tgtgaattgg tgggtagtga gaatggaaaa ttcatggaga      540
aaattcatta tgaaaaatct gaaaaatgga atgaaaaatt ataccgcgaa agtttccaga      600
acacggtgaa gtcataatac atacaaacag ttggaacatg acagaaccaa cacgaacacg      660
gagctaacca tcttatatgt cagacatcca actctagaga cattctagat gatcaagatc      720
gtcatccttt ccactcccat tacaaaacct cattacatct cattagtcaa agtccactca      780
ccgtccaccg cgcctggaac caagttgccc aatccggcca caccaggccc agtgtgctcc      840
caaaggtcga ctttgtcccg cgcctgcaca cagtccccac actaatcgaa tttcggttgg      900
ttcaccccca ctaagcacag gtgggctagt gccgggtata aagtaggga gagatccagt      960 aatccagcac ttgaaaaatt ctgttctgtt ttactcaatt cctcaattcc acatcac        1017

<210> SEQ ID NO 7
<211> LENGTH: 1043
<212> TYPE: DNA
<213> ORGANISM: Pichia stipitis
```

```
<400> SEQUENCE: 7
agatgactct gtagaaagtt gagtcaaatg ctgattaatt tggttctatt atgcctctcg      60
tagaagattg caaaagagca actgatgag gtgctatcaa gtgatgcgaa gagaacctgc      120
aaacaggcca gagtacatgc cgtgggttga tctctggtcg agtgtgctgg ctacagcctt     180
aagtacggag agtacagcta cagggtggtt tttgctgggc tacagcattg cagtttgaag     240
gttagagtgt agaatgtagc agacggctta aggctggtgg agtttagtcg aaactcgtta     300
gtatttccgt gaaggcagcc attgtgaaaa ttgaacatca cctgaggtat tttagccacc     360
agaagcggcg gtacggaaga aagtgtgtac aatggttggt ggtggaattg cgtgcatgcc     420
tgatggggca atattaatta gatagagctt tggtgatatt agtggataat agaattcaca     480
gagaagacat caggagcaat ttccaagagc cattgatgat gtaattgccc caacagcaag     540
attcagatct gacaattgac caccgttttg tagaagcaaa aaatcgtaga ttatcaccaa     600
gagggttttt caccgaacca gcaaatagaa actattccgt agaactcgcc caggcttttt     660
tgctagcact ttccagcagt agaaccgtcc aattaagtca acaggaacca ttgaggtcga     720
gcccaaccac ctgaaccccc tcacggtcgt gtccctatta ttgatccaga gggtgccagt     780
ttcggtagcc aatattggtt catgggtttc tatggcccgg agtgagtttg caggttggcc     840
ccggcgccgt ctgcaggatg ggagttatag cggccaaact tcacatttcg aaatcctgct     900
gcagccaatc tgaagaatta atataaattc gtgtcgaatc gccgtctgtg aaatttcagt     960
acttgatttt cttttcttct tcttttttctc ttttgtttct tcagaatcaa ttcacatttt     1020
ttcttcccta taaacaattc atc                                             1043

<210> SEQ ID NO 8
<211> LENGTH: 35
<212> TYPE: DNA
<213> ORGANISM: Pichia stipitis

<400> SEQUENCE: 8
gattacatgt taacgattgt tcgacgcaac taccc                                35

<210> SEQ ID NO 9
<211> LENGTH: 36
<212> TYPE: DNA
<213> ORGANISM: Pichia stipitis

<400> SEQUENCE: 9
gattacatgt taaccttccc caacaagacc gaattg                               36

<210> SEQ ID NO 10
<211> LENGTH: 21
<212> TYPE: DNA
<213> ORGANISM: Pichia stipitis

<400> SEQUENCE: 10
ttaaaacaag aatttgggga g                                               21

<210> SEQ ID NO 11
<211> LENGTH: 27
<212> TYPE: DNA
<213> ORGANISM: Pichia stipitis

<400> SEQUENCE: 11
aaaggtctaa ttattcaatt tatcgac                                         27
```

<210> SEQ ID NO 12
<211> LENGTH: 1653
<212> TYPE: DNA
<213> ORGANISM: Pichia stipitis

<400> SEQUENCE: 12

```
atgtcctcac aagatttacc ctcgggtgct caaaccccaa tcgatggttc ttccatcctc      60
gaagataaag ttgagcaaag ttcgtcctca aatagccaaa gtgatttagc ttccattcca     120
gcaacaggta tcaaagccta tctcttggtt tgtttcttct gcatgttggt tgcctttggt     180
ggattcgtat tcggtttcga taccggtaca atttccggtt tccttaatat gtctgatttc     240 cttttccagat ttggtcaaga tggttctgaa ggaaaatatt tgtctgatat cagagtcggt     300
ttgattgttt ccattttaa cattggttgt gcaattggtg gtatttttcct ttctaagata     360 ggagatgttt acggtagaag aattggtatc atttcagcta tggttgtcta cgtcgtcggt     420
attatcatcc agatctcgtc ccaagacaag tggtaccaac ttacaattgg acgtggagtt     480
acaggattag ctgttggtac tgtttcagtg ttgtctccaa tgttcattag tgaaagtgct     540
ccaaagcatt tgagaggtac tttggtatac tgttaccaat tatgtatcac cttaggtatt     600
ttcattggtt actgtgtcac ttatggaacc aaagatttaa atgattcaag acaatggaga     660
gttcctttgg gtttatgttt cctttgggct attttcttag ttgtcggtat gttggctatg     720
cctgaatccc caagattctt aattgaaaag aagagaatcg aagaagccaa gaagtccctt     780
gcaagatcca acaagttatc tccagaagat ccaggtgtct cactgaagt tcaattgatt     840 caggctggta ttgacagaga agctgctgca ggttctgctt catggatgga attgatcact     900
ggtaagccag ctatttcag aagagttatc atgggaatta tcttacagtc tttgcaacaa     960
ttaactggtg tcaactattt cttctattac ggaactacaa tcttccaagc tgttggtttg    1020
caagattcct tccagacttc catcatctta ggtacagtca actttctttc tacatttgtt    1080
ggtatttggg ccattgaaag atttggaaga agacaatgtt tgttagtcgg ttctgctggt    1140
atgttcgttt gtttcatcat ttactccgtt attggtacaa ctcatttgtt cattgatgga    1200
gtagtagata cgacaacac ccgtcaactg tctggtaatg ctatgatctt tatcacttgt    1260
ttgttcatct tcttcttgc ctgtacatgg gctggaggtg ttttttaccat catttccgaa    1320 tcatatccat tgagaatcag atccaaggca atgtctattg ctactgctgc taactggatg    1380
tggggcttct tgatttcctt ctgcactcca ttcattgtta atgccatcaa cttcaagttc    1440
ggctttgtgt ttactggttg tttactcttt tcgttcttct atgtctactt ctttgtcagc    1500
gaaaccaaag gtttgtcgtt ggaagaagtt gatgagttgt acgctgaagg tattgcacca    1560
tggaagtctg gtcatgggt tcctccttct gcccaacaac aaatgcaaaa ctccacttat    1620
ggtgccgaag caaaagagca agagcaagtt tag                                 1653
```

<210> SEQ ID NO 13
<211> LENGTH: 1656
<212> TYPE: DNA
<213> ORGANISM: Pichia stipitis

<400> SEQUENCE: 13

```
atgtcctcac aagatttacc ctcgggtgct caaaccccaa tcgatggttc ttccatcctc      60
gaagataaag ttgagcaaag ttcgtcctca aatagccaaa gtgatttagc ttccattcca     120
gcaacaggta tcaaagccta tctcttggtt tgtttcttct gcatgttggt tgcctttggt     180
ggcttcgtat tcggtttcga taccggtaca atttccggtt tccttaatat gtctgatttc     240 cttttccagat ttggtcaaga tggttctgaa ggaaaatatt tgtctgatat cagagtcggt     300
```

```
ttgattgttt ccatttttaa cattggttgt gcaattggtg gtattttcct ttctaagata    360
ggagatgttt acggtagaag aattggtatc atttcagcta tggttgtata cgtcgtcggt    420
attatcatcc agatctcgtc ccaagacaag tggtaccaac ttacaattgg acgtggagtt    480
acaggattag ctgttggtac tgtttcagtg ttgtctccaa tgttcattag tgaaagtgct    540
ccaaagcatt tgagaggtac tttggtatac tgttaccaat tatgtatcac cttaggtatt    600
ttcattggtt actgtgtcac ttatggaacc aaagatttaa atgattcaag acaatggaga    660
gttcctttgg gcttatgctt cctttgggct attttcttag ttgtcggtat gttggctatg    720
ccagaatccc caagattctt aattgaaaag aagagaatcg aagaagccaa gaagtccctt    780
gcaagatcca acaagttatc tccggaagat ccaggtgtct acactgaact tcaattgatt    840
caggctggta ttgacagaga agctgctgca ggttctgctt cgtggatgga attgatcact    900
ggtaagccag ctattttcag aagagttatc atgggaatta tcttgcagtc tttgcaacaa    960
ttaactggtg tcaactattt cttctattac ggaactacaa tcttccaagc tgttggtttg   1020
caagattcct tccagacttc catcatctta ggtacagtca actttctttc tacatttgtt   1080
ggtatttggg ccattgaaag atttggaaga agacaatgtt tgttagtcgg ttctgctggt   1140
atgttcgttt gtttcatcat ttactccgtt attggtacaa ctcatttgtt cattgatgga   1200
gtagtagata acgacaacac ccgtcaactg tctggtaatg ctatgatctt tatcacttgt   1260
ttgttcatct tcttctttgc ctgtacatgg gctggaggtg tttttaccat catttccgaa   1320
tcatatccat tgagaatcag atccaaggca atgtctattg ctactgctgc taactggatg   1380
tggggcttct tgatttcctt ctgcactcca ttcattgtta atgccatcaa cttcaagttc   1440
ggctttgtgt ttactggttg tttactcttt tcgttcttct atgtctactt ctttgtcagc   1500
gaaaccaaag gtttgtcgtt ggaagaagtt gatgagttgt acgctgaagg tattgcacca   1560
tggaagtctg gtgcatgggt tcctccttct gcccaacaac aaatgcaaaa ctccacttat   1620
ggtgccgaag caaaagagca agagcaagtt tagstt                             1656
```